(12) United States Patent
Garrison et al.

(10) Patent No.: US 6,425,916 B1
(45) Date of Patent: Jul. 30, 2002

(54) METHODS AND DEVICES FOR IMPLANTING CARDIAC VALVES

(76) Inventors: Michi E. Garrison, 212 Roosevelt Blvd., Half Moon Bay, CA (US) 94019; Hanson S. Gifford, III, 3180 Woodside Rd., Woodside, CA (US) 94062; Frederick G. St. Goar, 2 Frederick Ct., Menlo Park, CA (US) 94025

( * ) Notice: Subject to any disclaimer, the term of this patent is extended or adjusted under 35 U.S.C. 154(b) by 0 days.

(21) Appl. No.: 09/248,911

(22) Filed: Feb. 10, 1999

(51) Int. Cl.[7] .................................................. A61F 2/24
(52) U.S. Cl. ..................... 623/2.11; 623/1.26; 623/2.38; 623/904
(58) Field of Search ............................... 623/1.26, 1.24, 623/2.11, 2.1, FOR 101, 2.12–2.19, 2.42, 904, 2.38

(56) References Cited

FOREIGN PATENT DOCUMENTS

EP          0850607 A1  *  7/1998   ........ 623/FOR 101

* cited by examiner

Primary Examiner—David H. Willse

(57) ABSTRACT

The valve implantation system has a valve displacer for displacing and holding the native valve leaflets open in a first aspect of the invention. A replacement valve may be attached to the valve displacer before or after introduction and may be positioned independent of the valve displacer. In another aspect of the invention, the valve displacer and valve are in a collapsed condition during introduction and are expanded to deploy the valve displacer and valve. The valve is a tissue valve mounted to an expandable support structure. The support structure may have protrusions for engaging the valve displacer or barbs for anchoring the valve displacer to the heart or blood vessel. A temporary valve mechanism may be used to provide temporary valve functions during and after deployment of the valve displacer.

16 Claims, 23 Drawing Sheets

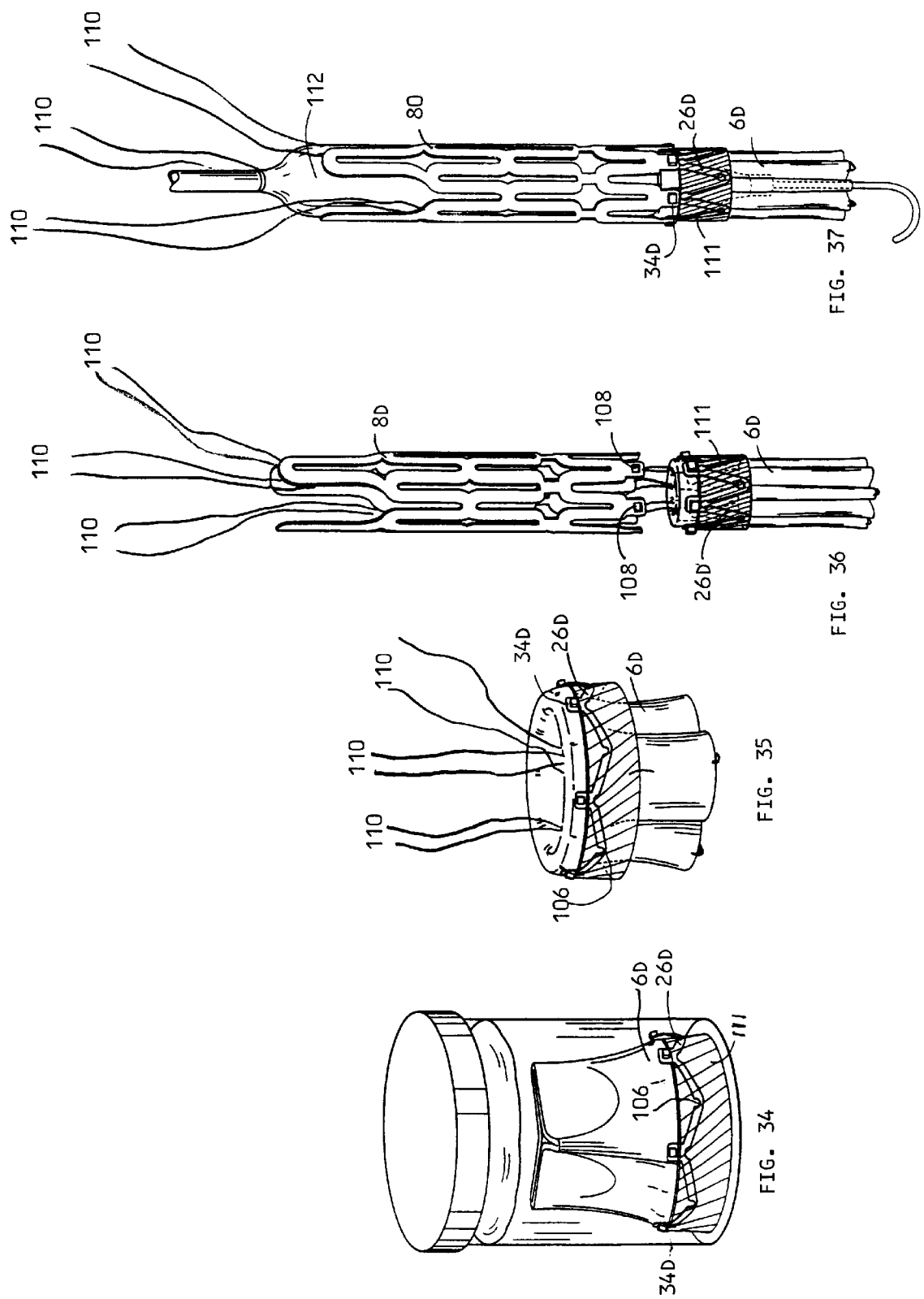

METHODS AND DEVICES FOR IMPLANTING CARDIAC VALVES

BACKGROUND OF THE INVENTION

The present invention is directed to methods and devices for implanting replacement cardiac valves. Replacement cardiac valves are implanted when the patient's native valve exhibits abnormal anatomy and function due to congential or acquired valve disease. Congenital abnormalities can be tolerated for years only to develop into life-threatening problems later. Acquired valve disease may result from various causes such as rheumatic fever, degenerative disorders of the valve tissue, and bacterial or fungal infections.

Valve dysfunction can be classified as either stenosis, in which the valve does not open properly, or insufficiency, in which the valve does not close properly. Stenosis and insufficiency can occur at the same time and both abnormalities increase the workload on the heart in pumping blood through the body. The ability of the heart to function with the increased workload is a major factor in determining whether the valve should be replaced.

When the valve must be replaced using conventional methods, the patient must undergo an invasive, traumatic surgical procedure. The patient's chest is opened with a median sternotomy or major thoracotomy to provide direct access to the heart through the large opening in the chest. The heart is then stopped and the patient is placed on cardiopulmonary bypass using catheters and cannulae inserted directly into the heart and great vessels. The heart, or a great vessel leading to the heart, is then cut open to access and remove the malfunctioning valve. After removing the valve, the replacement valve is then sewn into place. After the new valve has been implanted, the chest is then closed and the patient is weaned off cardiopulmonary bypass support.

The conventional open-chest surgery described above is problematic in that it is highly invasive, traumatic and requires a lengthy recovery time. These drawbacks to conventional open-chest surgery prevent some patients from undergoing a valve implantation procedure even though a new cardiac valve is needed.

U.S. Pat. Nos. 5,370,685, 5,411,552 and 5,718,725, which are hereby incorporated by reference, describe devices and methods for implanting a new cardiac valve without requiring a median sternotomy or major thoracotomy. Such devices and methods reduce the pain, trauma and recovery time as compared to conventional open-chest surgery.

An object of the present invention is to provide additional devices and methods which reduce the trauma associated with conventional open-chest methods and devices for implanting cardiac valves.

SUMMARY OF THE INVENTION

In accordance with the object of the invention, a system and method for implanting a cardiac valve is provided which does not require a median sternotomy or major thoracotomy. The devices and methods of the present invention are preferably carried out by passing the valve through a blood vessel, preferably the femoral artery, so that the median sternotomy or major thoracotomy is not required. Alternatively, the systems of the present invention also permit introduction of the valve through a small incision between the patient's ribs without cutting the ribs or sternum.

In a first aspect of the invention, a valve displacer is used to hold the native valve leaflets open so that the native valve does not need to be removed. The valve displacer is preferably introduced into the patient in a collapsed condition and expanded to displace and hold the leaflets open. The valve displacer may either be expanded with an expansion mechanism, such as a balloon, or may be self-expanding. In a preferred embodiment, the valve displacer has a first end, a second end and a central section between the first and second ends. The first and second ends are preferably flared outwardly to form a circumferential recess around the central portion. The native leaflets are trapped within the recess when the valve displacer is deployed.

In another aspect of the invention, the valve is also introduced into the patient in a collapsed condition and expanded within the patient. The valve may either be expanded with an expansion mechanism, such as a balloon, or may be self-expanding. The cardiac valve may be coupled to the valve displacer or may be positioned independent from the valve displacer while still substantially performing the functions of the native valve. For instance, a replacement aortic valve may be positioned in the ascending or descending aorta to substantially perform the functions of the native aortic valve.

The cardiac valve is preferably delivered separate from the valve displacer but may also be integrated with the valve displacer during introduction and deployment. In a preferred embodiment, the valve has protrusions which engage openings in the valve displacer. In another embodiment, the valve has sharp elements or barbs which either pierce the native valve tissue or engage the sides of the openings in the valve displacer.

In yet another aspect of the present invention, the valve and valve displacer are preferably introduced into the patient with a catheter system. In a preferred system, the valve displacer is mounted to a first catheter and the valve is mounted to a second catheter which passes through and is slidably coupled to the first catheter. Alternatively, the valve displacer and valve may be mounted to a single catheter. The term catheter as used herein refers to any catheter, trocar or similar device for introducing medical devices into a patient.

In still another aspect of the present invention, the valve delivery catheter has a temporary valve mechanism which provides temporary valve functions after deployment of the valve displacer. The temporary valve mechanism prevents regurgitation while the native valve is held open and before deployment of the replacement cardiac valve. The temporary valve mechanism is preferably a balloon which is inflated and deflated as necessary to permit downstream flow and prevent retrograde flow. Although it is preferred to implant the cardiac valve while the patient's heart is beating, the devices and methods of the present invention may also be used with the patient's heart stopped and the patient supported by a bypass system.

These and other advantages and aspects of the invention will become evident from the following description of the preferred embodiments and claims.

BRIEF DESCRIPTION OF THE DRAWINGS

FIG. 34 shows the valve being stored in a preservative solution.

FIG. 35 shows the valve inverted and in the expanded condition.

FIG. 36 shows the valve and valve displacer in the collapsed condition before being attached to one another.

FIG. 37 shows the valve and valve displacer attached to one another and mounted to the delivery catheter.

DESCRIPTION OF THE PREFERRED EMBODIMENTS

Figure 1A:
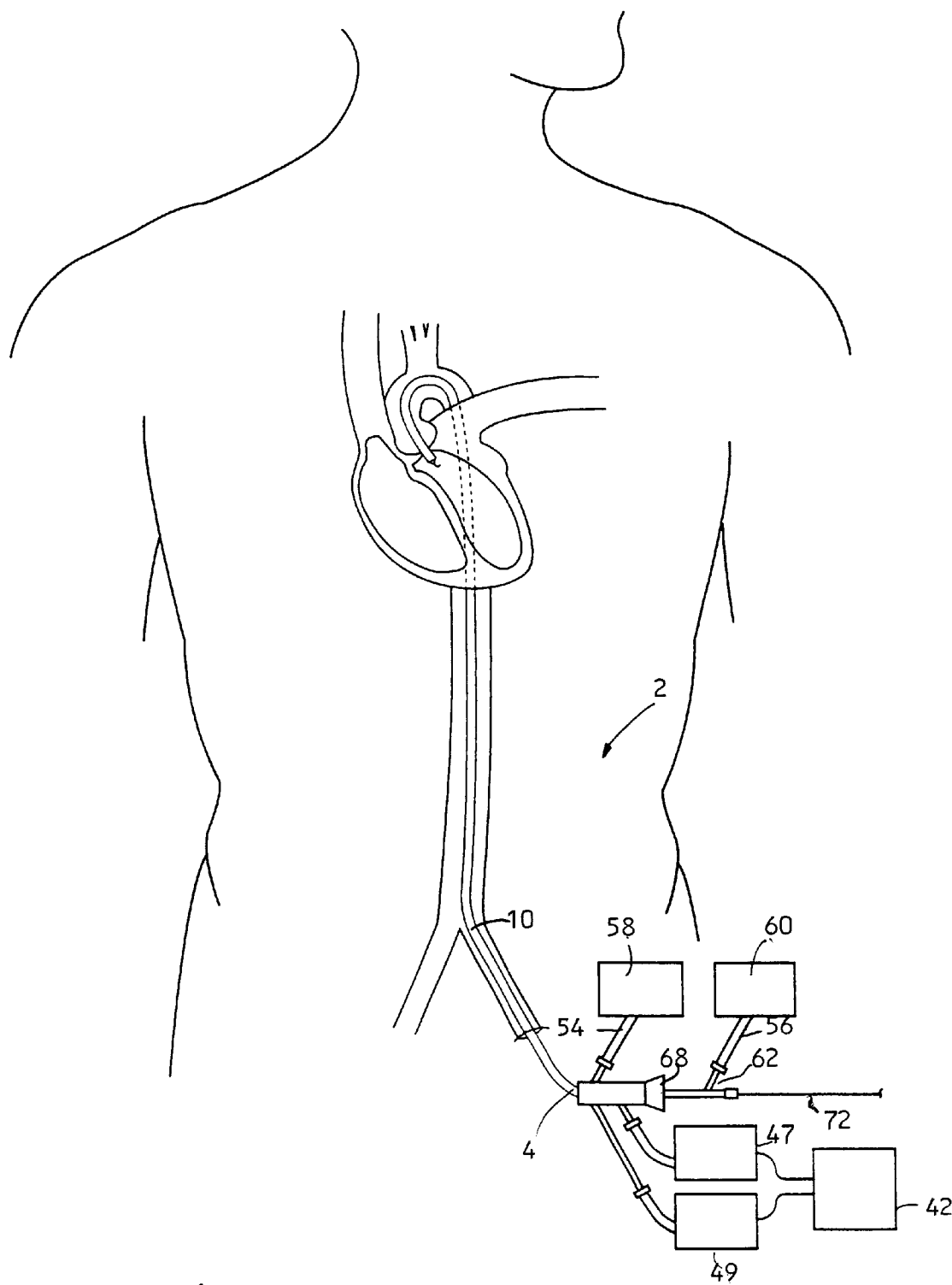
FIG. 1A shows a system for implanting a cardiac valve.
Figure 1B:
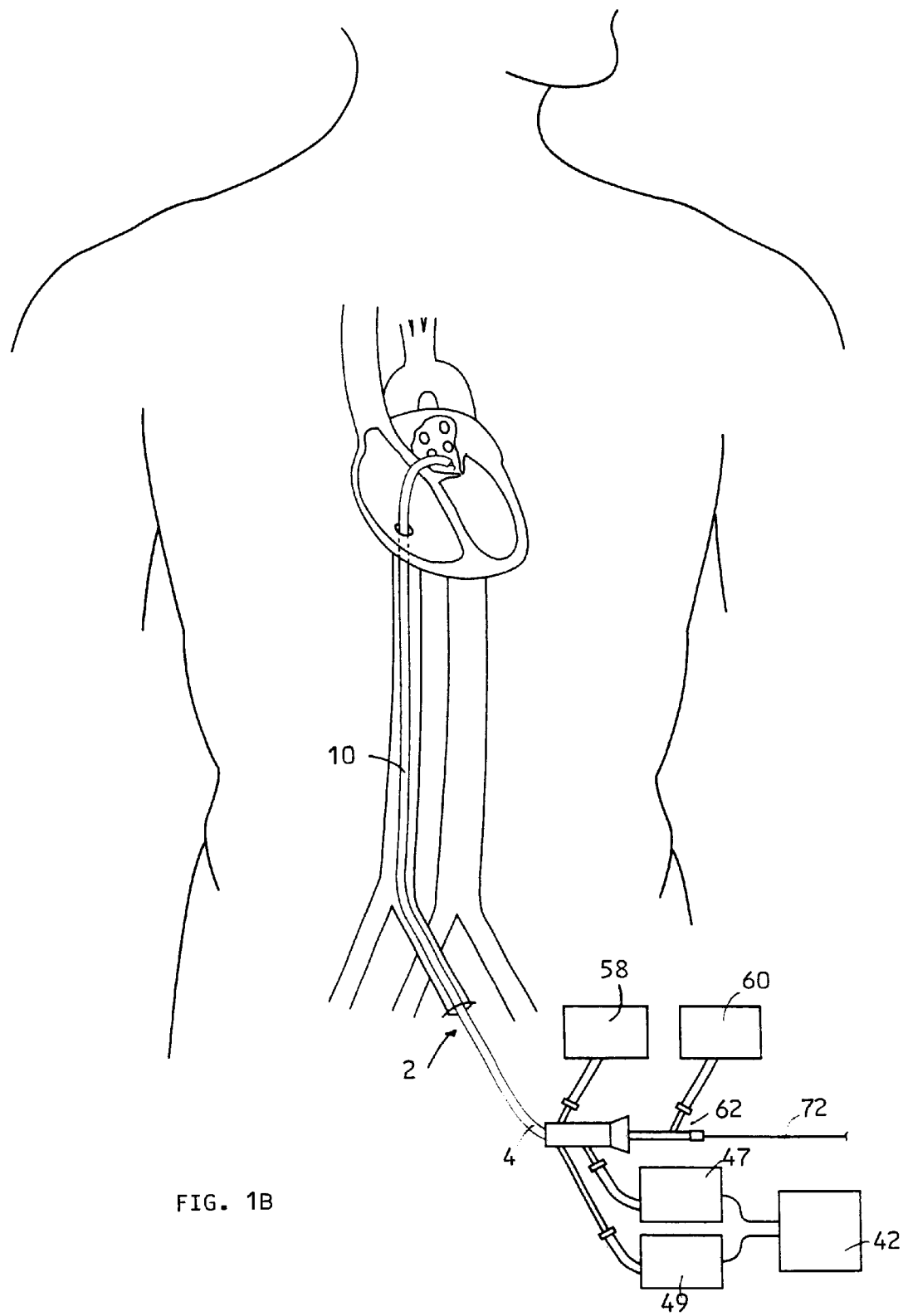
FIG. 1B shows the system of FIG. 1A introduced through a femoral vein.
Figure 2:
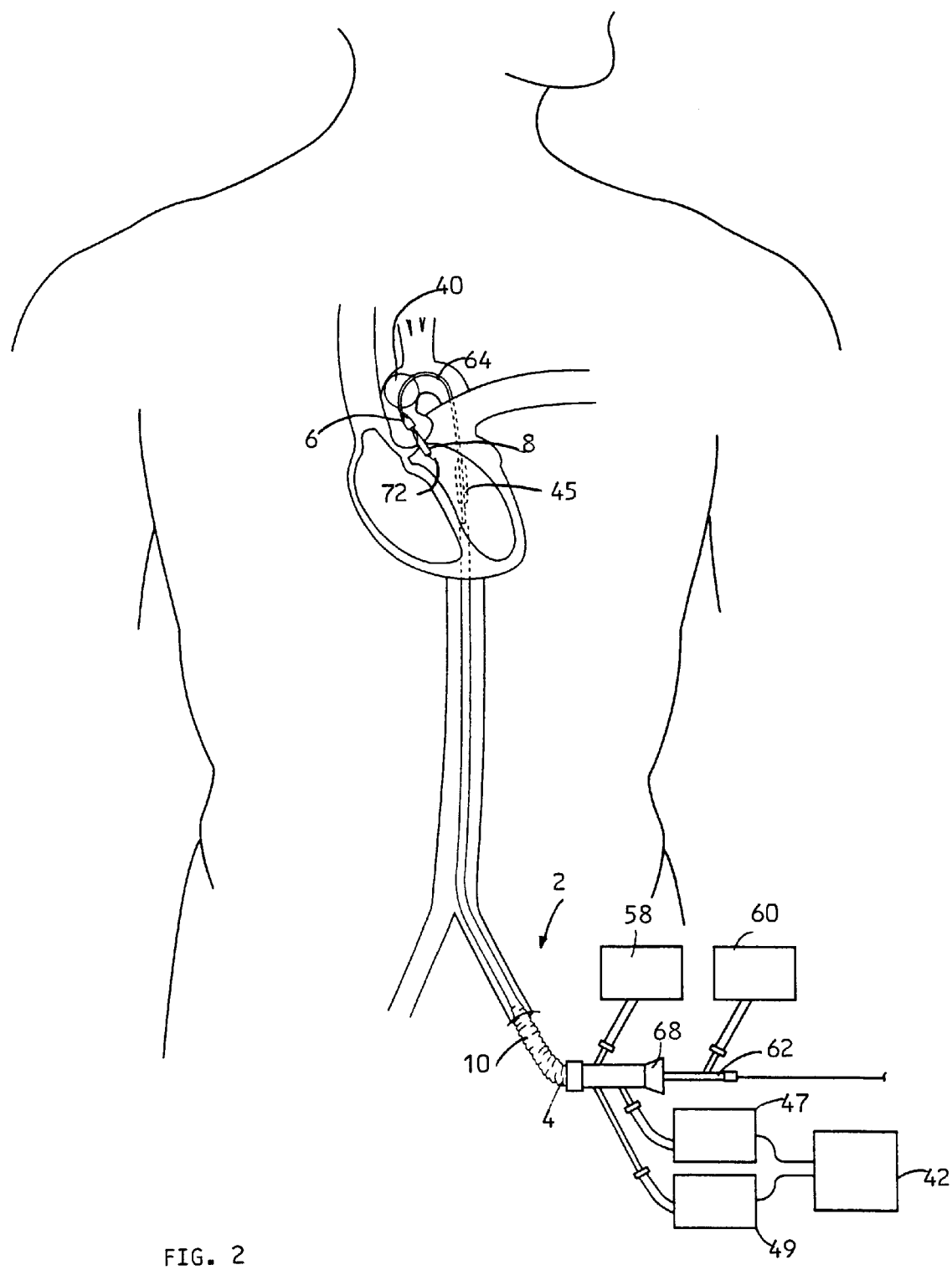
FIG. 2 shows the system of FIG. 1 with a sheath retracted to expose the cardiac valve, a valve displacer and a temporary valve mechanism.

Referring to FIGS. 1A. 1B and 2 a system for implanting a replacement cardiac valve is shown. The present invention is described in connection with implantation of a replacement aortic valve but is applicable to any other cardiac valve. The system 2 includes a delivery catheter 4, a cardiac valve 6 and a valve displacer 8. A protective sheath 10 covers the delivery catheter 4, cardiac valve 6 and valve displacer 8 during introduction to prevent contact between the blood vessel and the cardiac valve 6 and valve displacer 8. FIGS. 1A and 1B show the sheath 10 extending around the cardiac valve 6 and valve displacer 8 and FIG. 2 shows the sheath 10 retracted to expose the cardiac valve 6 and valve displacer 8.

The cardiac valve 6 is preferably introduced through a peripheral vessel such as the femoral artery (FIGS. 1A and 2) or femoral vein (FIG. 1B). FIG. 1B shows introduction of the catheter 2 through the femoral vein, into the right atrium, through the intraatrial septum and into the left atrium to access the mitral valve. The peripheral vessel is preferably a femoral vessel but may also be the internal jugular vein, subclavian artery, axillary artery, abdominal aorta, descending aorta or any other suitable blood vessel. As will be explained below, the delivery catheter 4 may be introduced by surgical cutdown or percutaneously using the Seldinger technique. An advantage of passing the catheter 4 through a peripheral vessel is reduced trauma to the patient as compared to the conventional open-chest procedure described above. Although it is preferred to deliver the cardiac valve 6 through a peripheral vessel, the cardiac valve 6 may also be introduced directly into the ascending aorta through a small incision between ribs. The system 2 of the present invention is small enough to deliver between the patient's ribs so that the advantages of the present invention over conventional open-chest surgery are provided even when introducing the catheter through an incision in the chest.

The valve displacer 8 is expanded within the native valve to hold the native cardiac valve leaflets 6 open. An advantage of the system 2 and method of the present invention is that the native valve does not need to be removed. The replacement cardiac valves described herein may, of course, also be used when removing the native valve rather than using the valve displacer 8. Furthermore, the valve displacer 8 and cardiac valve 6 may be integrated into a single structure and delivered together rather than separately. Thus, all features of any valve displacer described herein may also form part of any of the cardiac valves described herein without departing from the scope of the invention.

Figure 4:
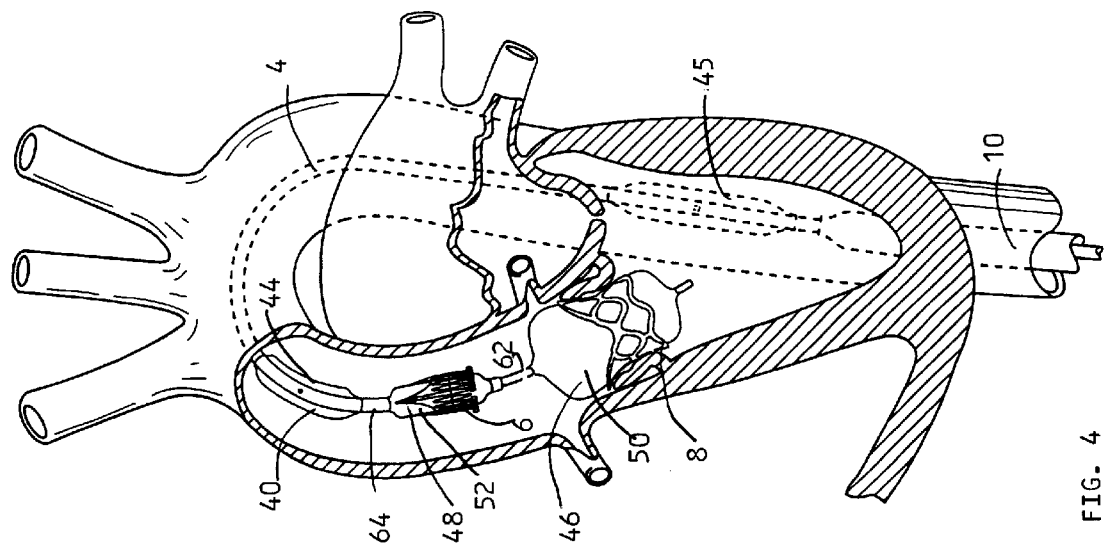
FIG. 4 shows the valve displacer expanded by a first expansion mechanism
Figure 3:
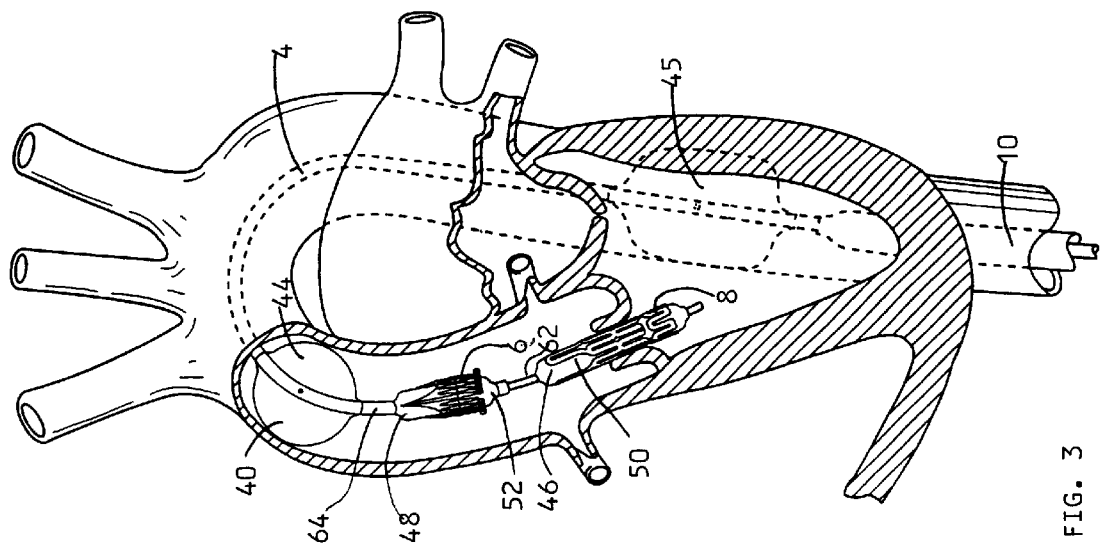
FIG. 3 shows the valve displacer positioned between the native valve leaflets prior to expansion.
Figure 6:
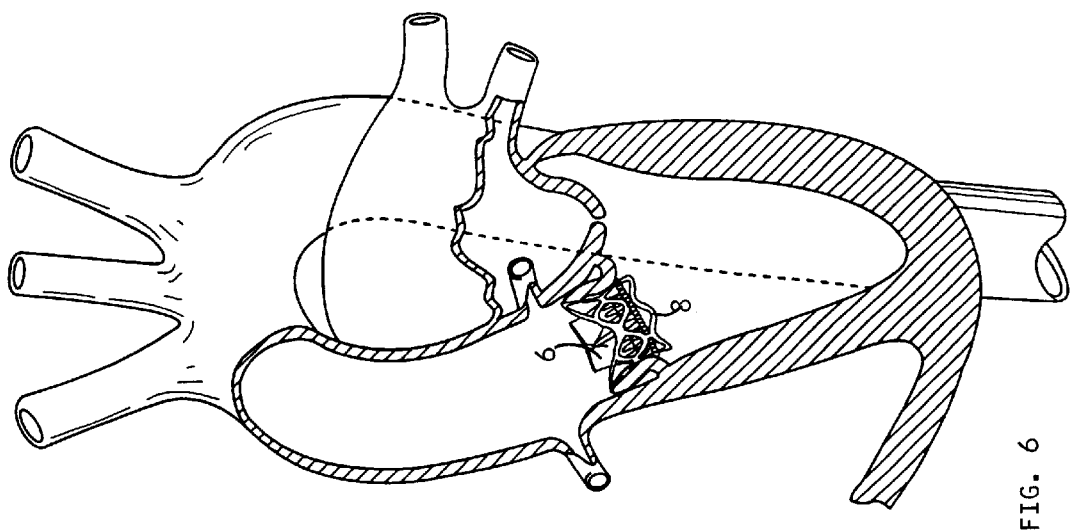
FIG. 6 shows the valve displacer and valve implanted in the native valve position.
Figure 7:
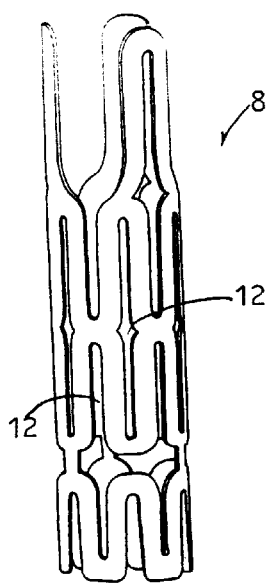
FIG. 7 shows the valve displacer in the collapsed position.
Figure 8:
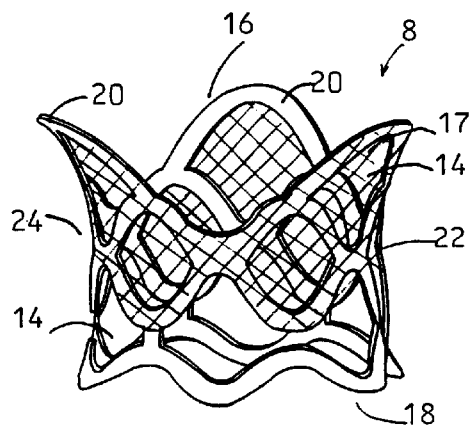
FIG. 8 shows the valve displacer in the expanded position.

The valve displacer 8 is shown in the collapsed condition in FIGS. 3 and 7 and in the expanded condition in FIGS. 4 and 8. When in the collapsed position, the valve displacer 8 forms a number of longitudinal slots 12 which form openings 14 in the valve displacer 8 when in the expanded condition. The valve displacer 8 is substantially cylindrical in the collapsed condition to facilitate introduction into the patient.

Referring to FIG. 8, first and second ends 16, 18 of the valve displacer 8 flare outwardly to form a circumferential recess 24 at a central section 22. The native leaflets are trapped in the recess 24 when the valve displacer 8 is deployed. The first end 16 has three extensions 20 extending from the central section 22. The valve displacer 8 may be made of any suitable material and preferred materials include stainless steel, nitinol, kevlar, titanium, nylon and composites thereof. The valve displacer 8 may also be coated with an antithrombogenic coating. The valve displacer 8 is preferably formed from a solid hypotube by etching or micromachining, machining from a solid material, or welding wire elements together. Although it is preferred to provide the flared ends 16, 18, the valve displacer 8 may have any other suitable shape which holds the leaflets open. The valve displacer 8 may also have a fabric cover 17 which can trap calcium fragments which might break free from the valve when the valve displacer is deployed. The cover 17 is preferably made of a polyesther knit material, such as dacron, but may be made of any other suitable material.

Figure 5:
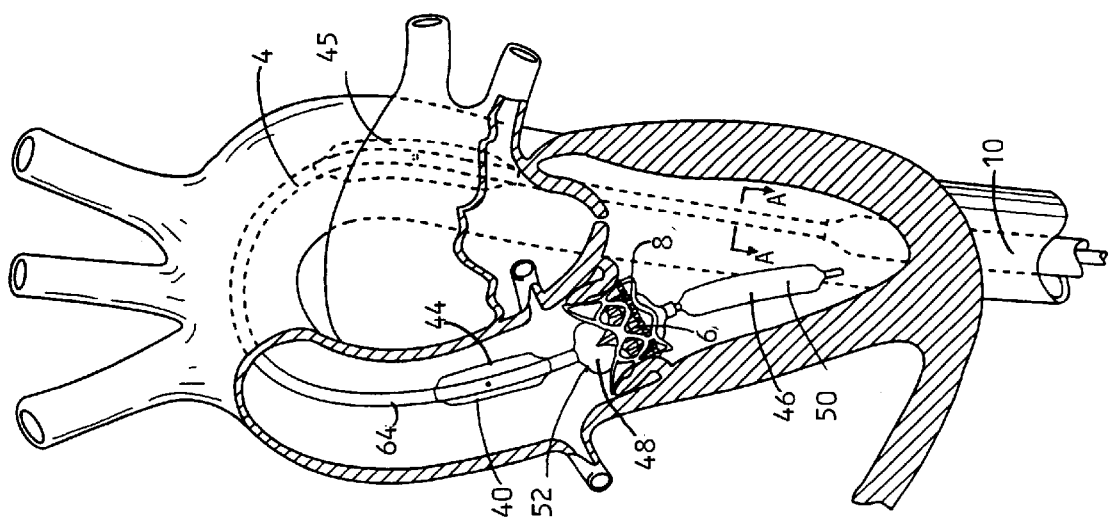
FIG. 5 shows the valve expanded by a second expansion mechanism into engagement with the valve displacer.
Figure 9:
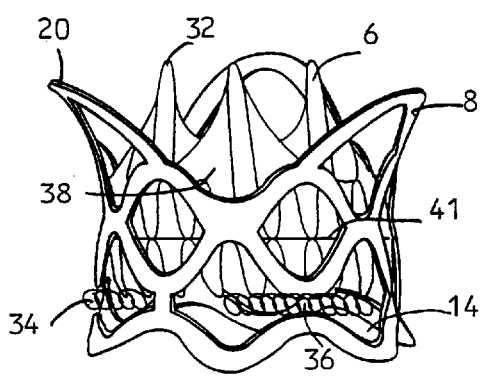
FIG. 9 shows the valve and valve displacer in the expanded position.
Figure 10:
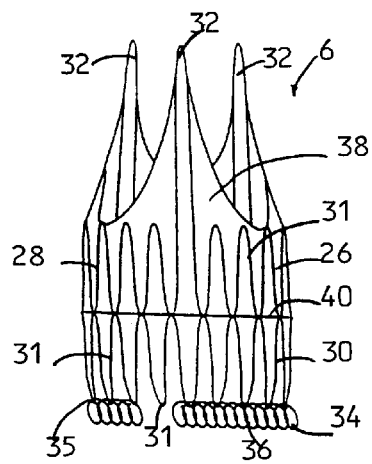
FIG. 10 shows the valve in a collapsed condition.

The cardiac valve 6 has an expandable support structure 26 which moves from the collapsed position of FIGS. 4 and 10 to the expanded position of FIGS. 5 and 9. The support structure 26 is preferably formed with first and second elongate members 28, 30 which are wound to form windings 31, preferably about 12–18 windings 31, around the circumference of the valve 6. The first and second elongate members 28, 30 are attached to one another at windings 31 which forms three posts 32 extending from the support structure 26.

The support structure 26 has a protrusion 34, preferably three, extending outwardly to form an interrupted lip around an end 35 of the support structure 26. The protrusions 34 engage the openings 14 in the valve displacer 8 as shown in FIG. 9 to secure the cardiac valve 6 to the valve displacer 8. The protrusions 34 are preferably formed by a coil 36 wrapped around the loops 31 in the elongate member 30. As will be described below, the support structure 26 may also have barbs to secure the cardiac valve 6 to the valve displacer 8 or to the blood vessel wall. The cardiac valve 6 may also engage the valve displacer 8 with any other suitable connection.

Figure 11:
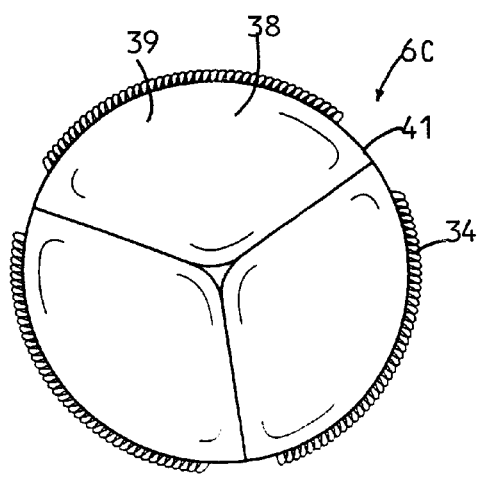
FIG. 11 is a plan view of the valve showing the leaflets.

The posts 32 support a valve portion 38 which performs the functions of the patient's malfunctioning native valve. Referring to FIGS. 10 and 11, the valve portion 38 is preferably a stentless tissue valve such as a tri-leaflet 39 stentless porcine valve. The valve portion 38 has a base 41 which is secured to the support structure 26 with sutures (not shown). The valve portion 38 may be stored separately from support structure 26 and attached to the support structure 26 before the procedure. Although it is preferred to provide a tissue valve for the valve portion 38, the valve portion 38 may also be made of a flexible, synthetic material. For example, the valve portion 38 may be made of polyurethane similar to the valves described in "A Tricuspid Polyurethane Heart Valve as Alternative to Mechanical Prostheses or Bioprostheses," by Lo et al., Trans Am Society of Artificial Internal Organs, 1988; 34: pgsvalve displacer 839–844, and "Evaluation of Explanted Polyurethane Trileaflet Cardiac Valve Prostheses," Journal Thoracic Cardiovascular Surgery, 1988; 94: pgs 419–429.

Referring to FIGS. 2–4, the delivery catheter 4 has a temporary valve mechanism 40 which provides temporary valve functions during and/or after deployment of the valve displacer 8. The temporary valve mechanism 40 ensures proper blood flow regulation when the leaflets are held open by the valve displacer 8 to provide time for accurate positioning and deployment of the valve 6. The temporary valve mechanism 40 is preferably a balloon 44 coupled to an inflation mechanism 47 controlled by a control system 42. The control system 42 senses the patient's heartbeat to time balloon inflation and deflation to permit and prevent flow in the same manner as the native valve. Similar systems for synchronizing inflation and deflation of a balloon with the patient's heartbeat are known in balloon pump technology and are described in U.S. Pat. Nos. 5,817,001, 5,413,549 and 5,254,097 which are hereby incorporated by reference. The balloon 44 is preferably inflated with a gas for quick inflation and deflation. The temporary valve mechanism 40 is preferably the balloon 44 but may also be a passive mechanical valve which automatically opens and closes due to blood flow forces.

The catheter 4 may also include an elongate balloon 45 to help pump blood through the patient's body like a blood pump. The balloon 45 is also coupled to an inflation mechanism 49 controlled by the control system 42 which inflates and deflates the balloon 45 to provide pumping assistance to the patient's heart. Balloon pump technology is described in the above-mentioned patents. The elongate balloon 45 may be replaced by any other suitable blood pump, such as a centrifugal pump having an impeller, without departing from the scope of the invention.

The temporary valve mechanism 40 and balloon 45 are, of course, only necessary when implanting the valve with the patient's heart beating. If the patient's heart is stopped and the patient is supported by a bypass system during the valve implantation procedure, the temporary valve mechanism 40 and/or balloon 45 may be used after the procedure for emergency valve functions or pumping assistance. The balloon 44 is preferably positioned in the ascending or descending aorta and the balloon 45 is preferably positioned in the descending aorta.

Referring to FIGS. 3–6. the delivery catheter 4 also has first and second expandable members 46, 48 which deploy the valve displacer 8 and cardiac valve 6. respectively. The expandable members 46, 48 are preferably balloons 50, 52 but may also be mechanically actuated devices. The balloons 50, 52 are coupled to inflation lumens 54, 56 through which inflation fluid is delivered from sources of inflation fluid 58, 60, respectively. The balloon 50 expands greater at the ends to form the flared ends 16, 18 of the valve displacer 8.

Figure 12:
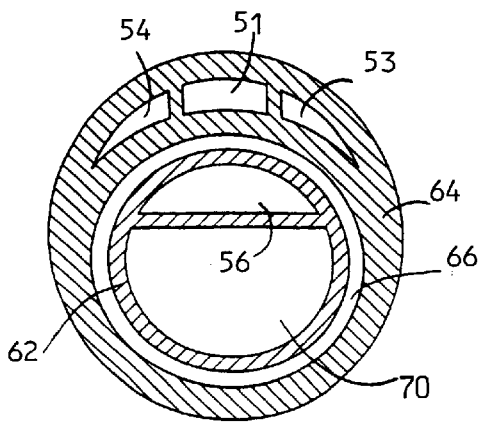
FIG. 12 is a cross-sectional view of the catheter along line A—A of FIG. 5.

The delivery catheter 4 includes a first catheter 62, which carries the valve displacer 8, and a second catheter 64, which carries the cardiac valve 6. Referring to FIGS. 2 and 12, the second catheter 64 has a passageway 66 which receives the first catheter 62. A hemostasis valve 68 permits slidable movement between the first and second catheters 62, 64. The first catheter 62 has lumen 54 for inflating balloon 50 and the second catheter 64 has lumen 48 for inflating balloon 52. The second catheter 64 also has a lumen 51 for inflating balloon 44 and a lumen 53 for inflating balloon 45. The first catheter 62 also has a main lumen 70 which receives a guidewire 72.

The slidable connection between the first and second catheters 62, 64 permits introduction of the first catheter 62 over the guidewire 72 with the second catheter 64 being advanced over the first catheter 62 after the valve displacer 8 is in the ascending aorta. In this manner, the first catheter 62 may be advanced more easily over the guidewire 72 and through the patient's vasculature, such as around the aortic arch, as compared to a single, multichannel catheter having all features of the first and second catheters 62, 64. The first and second catheters 62, 64 may be wire-reinforced (not shown) catheters constructed in the manner described in Published PCT Application WO 97/32623 entitled "Cannula and Method of Manufacture and Use" which is hereby incorporated by reference.

A method of implanting a cardiac valve 6 in accordance with the present invention is now described in connection with FIGS. 1–6. Although the method is described in connection with the system described above, the method may be practiced with other suitable devices, including the devices and systems described below, without departing from the scope of the invention. Furthermore, the method is described in connection with replacing the aortic valve, however, the method may also be applied to other other cardiac valves such as the mitral, tricuspid and pulmonary valves.

Before implanting the cardiac valve 6, it may be desirable to perform valvuloplasty to break up pathologic adhesions between the native valve leaflets. Breaking up adhesions ensures that the valve displacer 8 expands fully to provide a large blood flow path. Valvuloplasty is preferably performed with a balloon which is inflated to open the leaflets and break the adhesions. The native cardiac valve and annulus are also sized to determine the proper size valve displacer 8 and cardiac valve 6. Sizing may be carried out using fluoroscopy, intravascular ultrasound or with any other suitable device during or after the valvuloplasty. Size parameters to consider include the cross-sectional profile through the valve, the length and size of the valve leaflets and position of the coronary ostia.

The delivery catheter 4 is preferably introduced into the patient by surgical cutdown in the femoral artery but may also be introduced percutaneously using the Seldinger technique. As mentioned above, the delivery catheter 4 may also be introduced into any other suitable vessel or through a small incision in the chest. The first and second catheters 62, 64 are advanced into the artery through the cutdown a short distance. The guidewire 72 is then advanced ahead of the first and second catheters 62, 64 up the descending aorta, around the aortic arch, into the ascending aorta and across the aortic valve. The first catheter 62 is then advanced over the guidewire 72 to the ascending aorta with the sheath 10 covering the first catheter 62 to prevent contact between the valve displacer 8 and the blood vessel or native valve. The second catheter 64 is then advanced over the first catheter 62 to position the cardiac valve 6 in the ascending aorta. The sheath 10 also prevents contact between the cardiac valve 6 and vessel wall when advancing the second catheter 64. The sheath 10 is then retracted as shown in FIG. 2 to expose the valve displacer 8 and the cardiac valve 6.

The valve displacer 8 is then introduced between the valve leaflets as shown in FIG. 3 and the balloon 50 is inflated to expand the valve displacer as shown in FIG. 4. The valve displacer 8 holds the native valve leaflets open so that the native valve does not have to be removed. When the valve displacer 8 has been deployed, the temporary valve mechanism 40 provides temporary valve functions by inflating and deflating the balloon 44 at appropriate times to permit and block flow in the same manner as the native valve. The balloon 45 may also be inflated and deflated to provide pumping assistance to the patient's heart during the procedure. Although the above-described method is performed with the patient's heart beating, the procedure may also be performed on a stopped heart with the patient supported by a bypass system.

The second catheter 64 is then advanced until the valve 6 is positioned adjacent the valve displacer 8. Although FIG. 5 shows the first catheter 62 extending into the left ventricle, the first catheter 62 may also be designed to be withdrawn into the passageway 66 of the second catheter 64 so that the first catheter 62 does not extend beyond the second catheter 64. The balloon 52 is then partially inflated so that the distal end of the valve 6 having the protrusions 34 expands. The second catheter 64 is then manipulated until the protrusions 34 engage the openings 14 in the valve displacer 8. The balloon 52 is then inflated further to expand the rest of the support structure 26. The catheters 62, 64 are then removed leaving the cardiac valve 6 in place.

Figure 13:
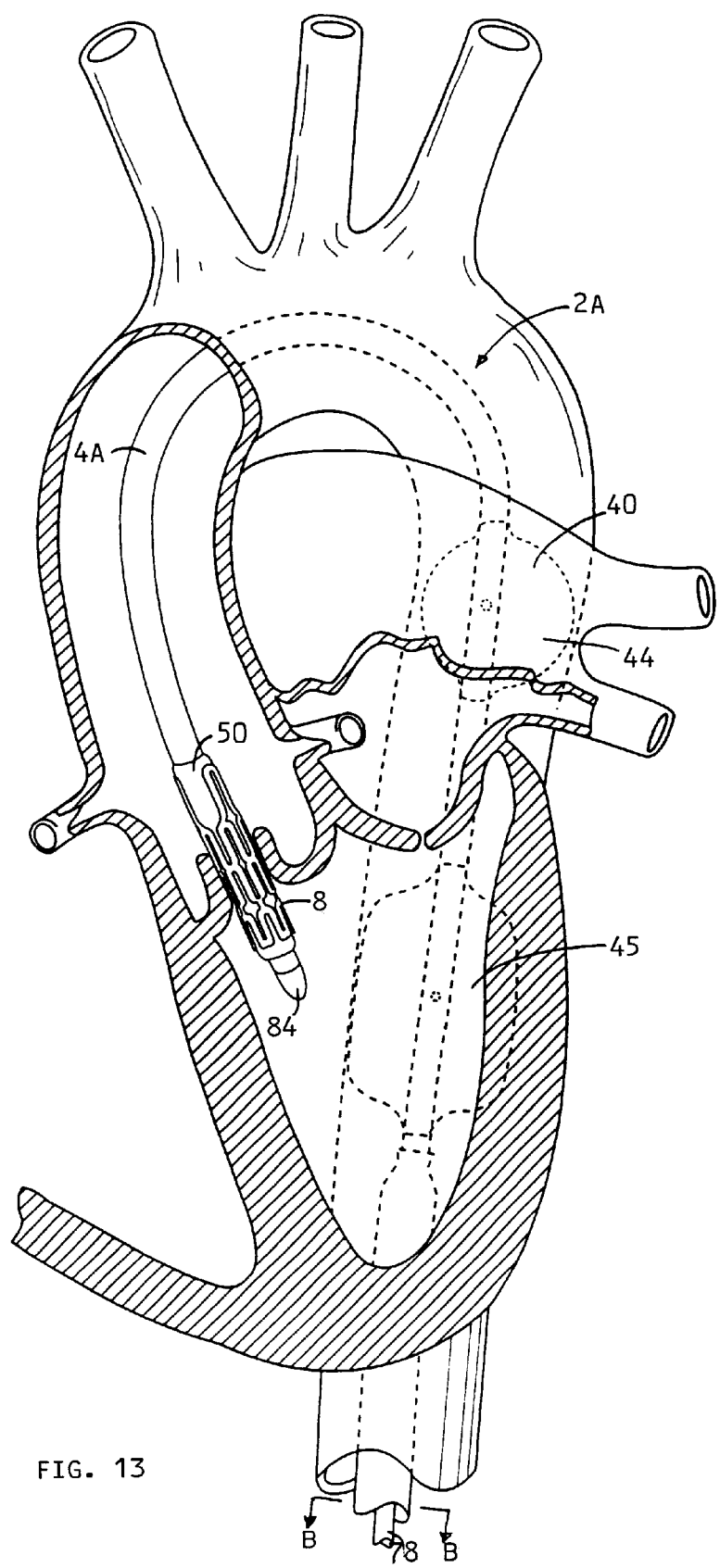
FIG. 13 shows another system for implanting another cardiac valve.
Figure 14:
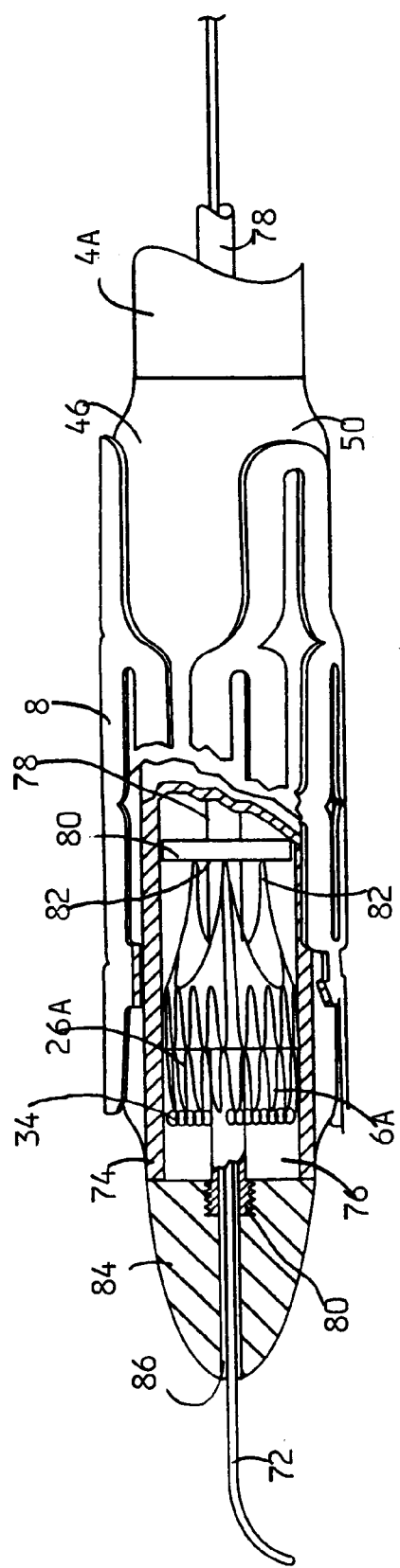
FIG. 14 is a partial cut-away view of the catheter of FIG. 13 with the valve contained in a chamber.

Referring to FIGS. 13 and 14, another system 2A for implanting a cardiac valve 6A is shown wherein the same or similar reference numbers refer to the same or similar structures. The cardiac valve 6A is similar to the cardiac valve 6 described above, however, the cardiac valve 6A is self-expanding and, therefore, does not require an independent expansion mechanism. The support structure 26A is made of a resilient material to naturally bias the support structure 26A to the expanded position. The support structure 26A may be made of any suitable material and preferred materials are stainless steel or shape-memory alloys such as nitinol. Delivery catheter 4A has the expandable member 46, which is preferably the balloon 50, for expanding the valve displacer 8.

Figure 15:
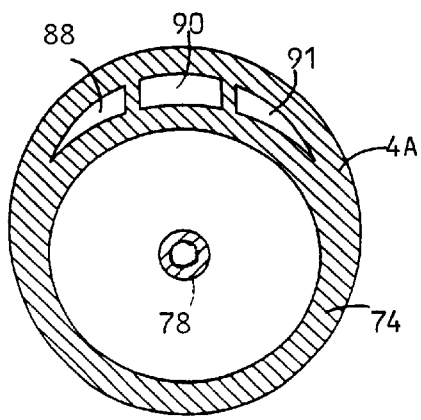
FIG. 15 is a cross-sectional view of the catheter along line B—B of FIG. 13.
Figure 29:
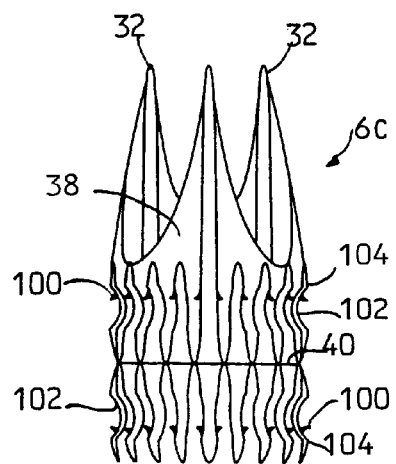
FIG. 29 shows the cardiac valve of FIGS. 23–28 in the collapsed condition.
Figure 30:
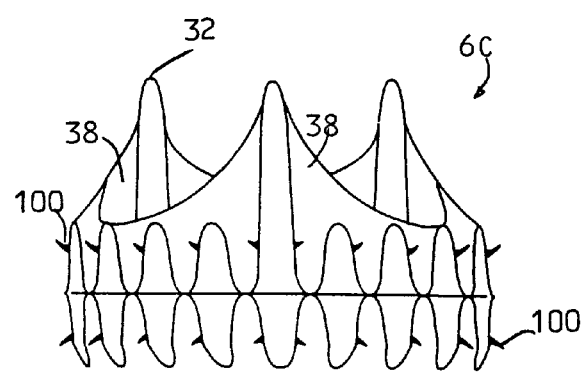
FIG. 30 shows the cardiac valve of FIGS. 23–28 in the expanded condition.

The cardiac valve 6A is contained within an outer wall 74 of the delivery catheter 4A. The cardiac valve 6A is advanced out of a chamber 76 in the delivery catheter 4A by advancing a rod 78 having a pusher element 80 attached thereto. The pusher element 80 engages the posts 82 on the cardiac valve 6A to move the cardiac valve 6A out of the chamber 76. The rod 78 has threaded connections 80, 82 with a tip 84 and the pusher element 80 to facilitate assembling the delivery catheter 4A and loading the cardiac valve 6A in the chamber 76. The rod 78 has a guidewire lumen 86 for receiving the guidewire 72. Referring to the cross-sectional view of FIG. 15, the catheter 4A has a first lumen 88 coupled to the balloon 50, a second lumen 90 coupled to the balloon 44 and a third lumen 91 coupled to the balloon 45. The second and third lumens 88, 90 are coupled to the inflation mechanisms 47, 29 which are controlled by the control system 42 described in connection with FIGS. 1 and 2. The system 2A preferably includes the sheath 10 which prevents contact between the blood vessel and the valve displacer 8 when the catheter 4A is advanced through the blood vessel.

The cardiac valve 6A is implanted in substantially the same manner as the cardiac valve 6 and the discussion of implantation of the cardiac valve 6 is also applicable here. The delivery catheter 4A may be introduced in any manner described herein and FIG. 13 shows the catheter 4A extending through the femoral artery with the valve displacer 8 positioned between the valve leaflets prior to expansion. The valve displacer 8 is expanded in the manner explained above to hold the leaflets open. After the valve displacer 8 has been expanded, the catheter 4A is retraced a predetermined amount so that the protrusions 34 are exposed outside the distal end of the catheter 4A. The catheter 4A may then be manipulated as necessary so that the protrusions 34 engage the openings 14 in the valve displacer 8. The valve 6A preferably remains coupled to the catheter 4A while the protrusions 34 are exposed for manipulation of the valve 6A until the valve 6A engages the valve displacer 8. After the valve 6A has engaged the valve displacer 8, the rod 78 is then advanced far enough to completely release the cardiac valve 6A.

Referring to FIGS. 16–22, another system 4B for implanting the cardiac valve 4A is shown wherein the same or similar reference numbers refer to the same or similar structure. The system has the self-expanding cardiac valve 4A described above. The valve displacer 8B is similar to the valve displacer 8 described above, however, the valve displacer 8B is also self-expanding and, therefore, does not require an independent expansion mechanism. The valve displacer 8B is made of a resilient material to naturally bias the valve displacer 8B to the expanded position. The valve displacer 8B may be made of any suitable material and preferred materials are stainless steel and shape-memory alloys such as nitinol.

Figure 16:
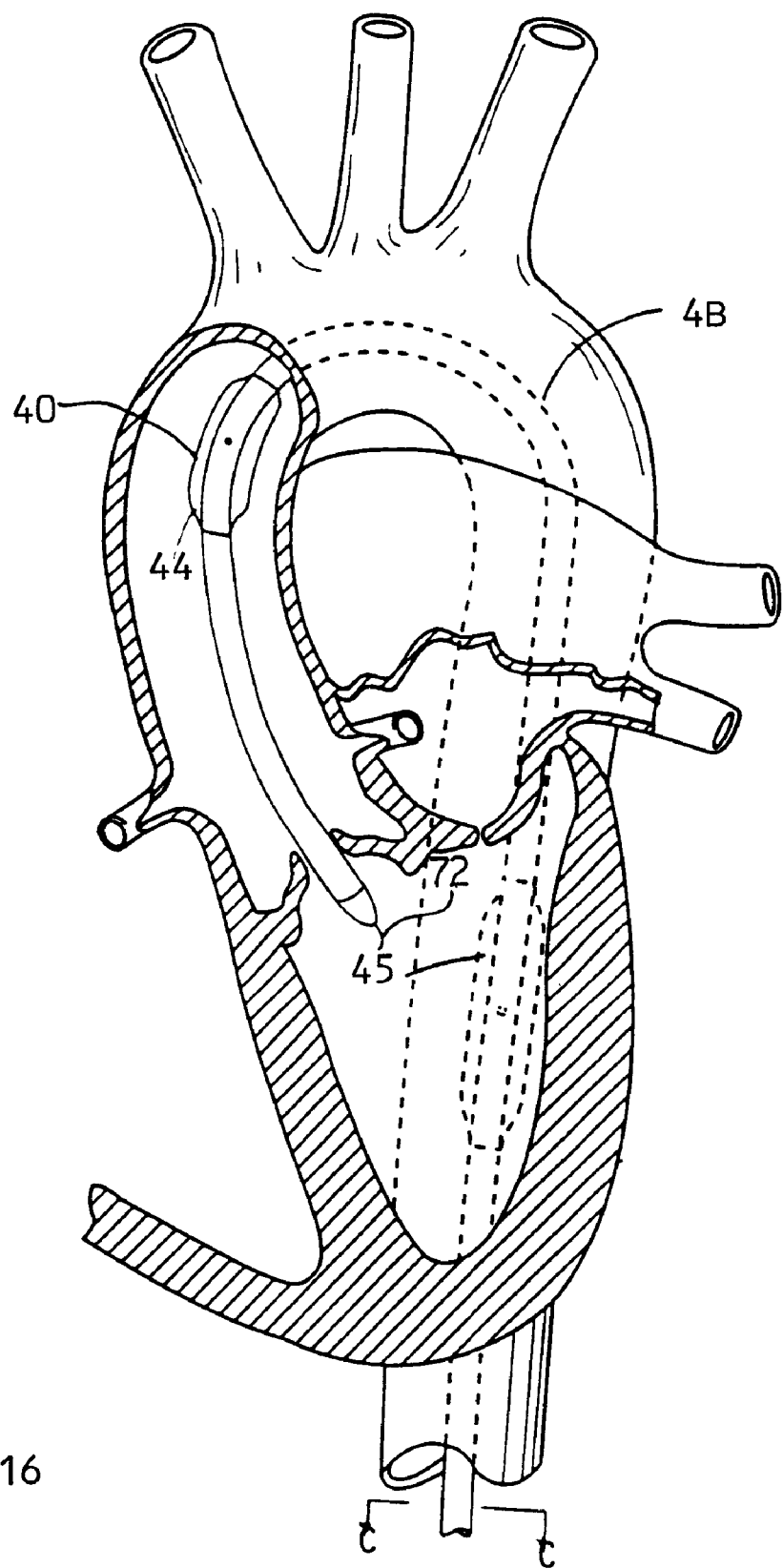
FIG. 16 shows another system for implanting a cardiac valve.
Figure 21:
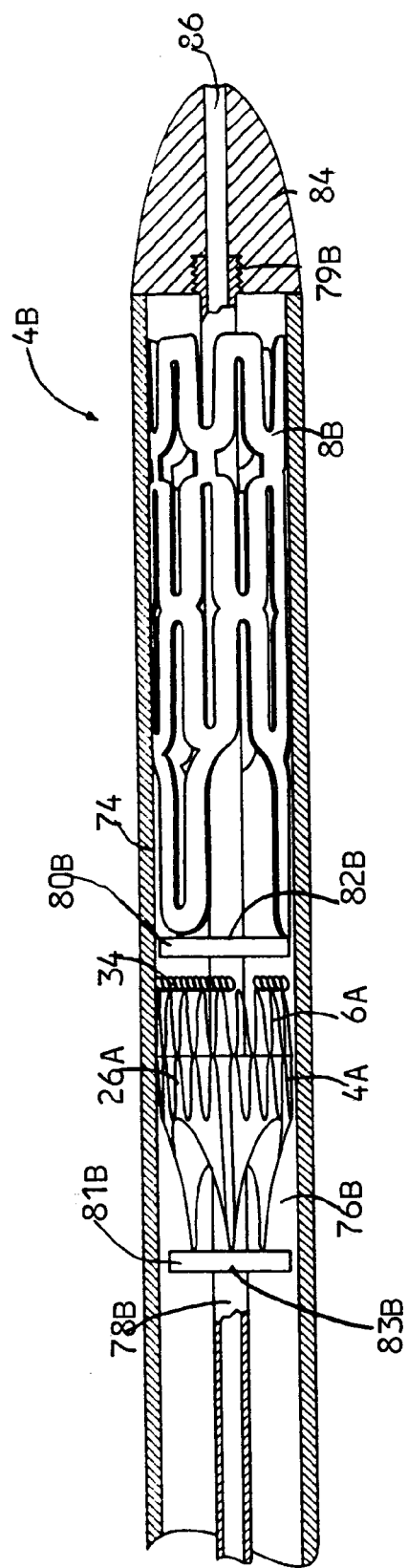
FIG. 21 is a partial cut-away view of the catheter of FIGS. 16–19.

The valve displacer 8B and cardiac valve 6A are contained within an outer wall 74 of the delivery catheter 4B as shown in FIG. 21. The valve displacer 8B and cardiac valve 4A are advanced out of a chamber 76B in the delivery catheter 4B by advancing a rod 78B having first and second pusher elements 80B, 81B attached thereto. The rod 78B has threaded connections 79B. 82B. and 83B with the tip 84 and the first and second pusher elements 80B, 81B to facilitate assembling catheter 4B and loading the valve displacer 8B and cardiac valve 6A in the chamber 76B. The rod 78B has the guidewire lumen 86 for receiving the guidewire 72 (FIG. 14). Referring to FIG. 16 and the cross-sectional view of FIG. 22. the catheter 4B has a lumen 90 coupled to the balloon 44 which serves as the temporary valve mechanism 40 and a lumen 93 which is coupled to the balloon 45. The lumen 90 and lumen 93 are coupled to the inflation mechanisms 47, 29 which are controlled by the control system 42 (FIGS. 1A, 1B, and 2).

Figure 18:
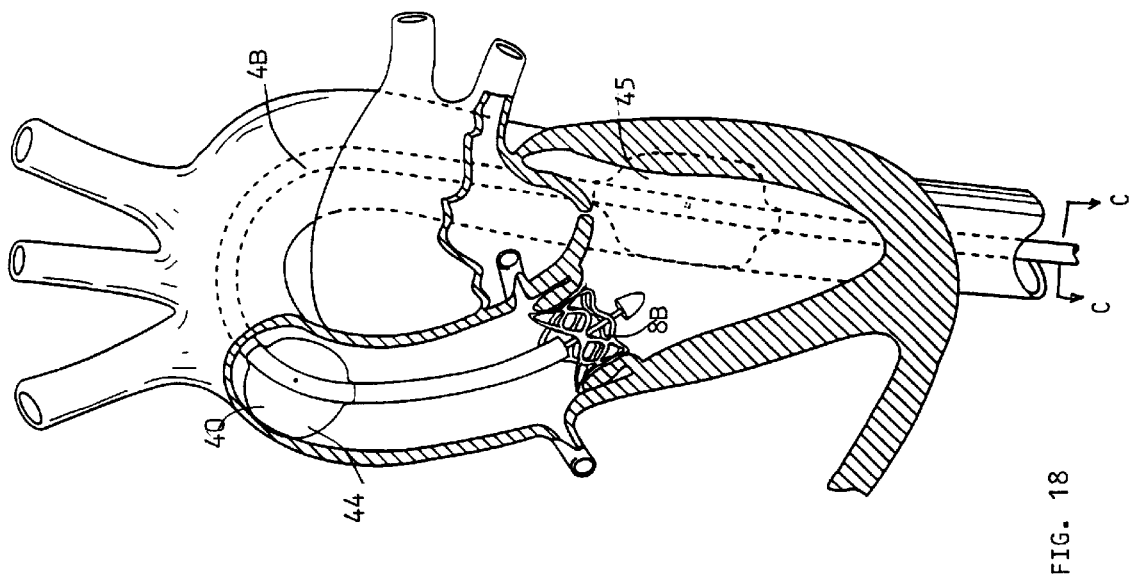
FIG. 18 shows the valve displacer fully deployed to hold the native leaflets open.
Figure 17:
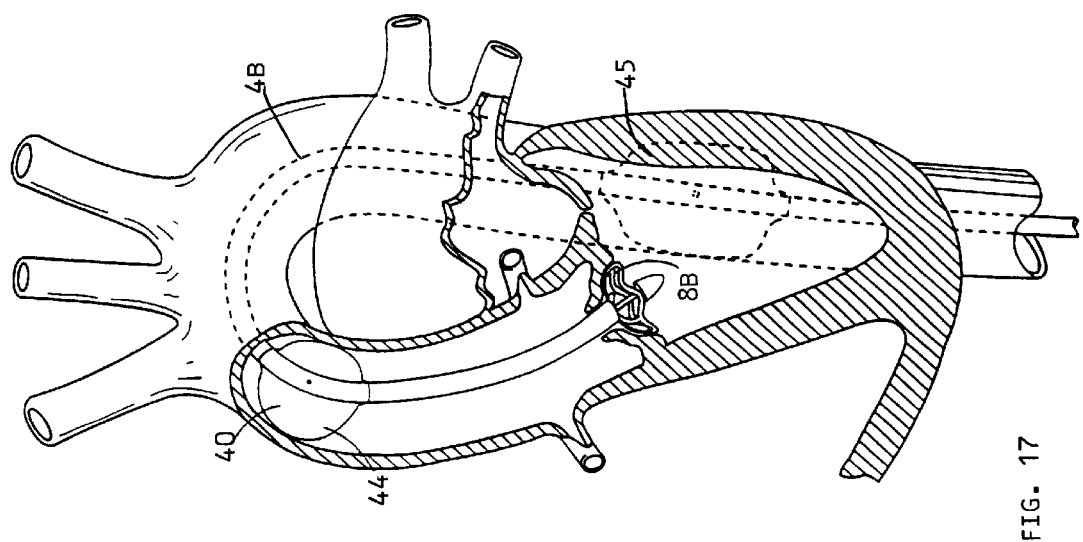
FIG. 17 shows the system of FIG. 16 with a distal portion of the valve displacer extending from the catheter.
Figure 19:
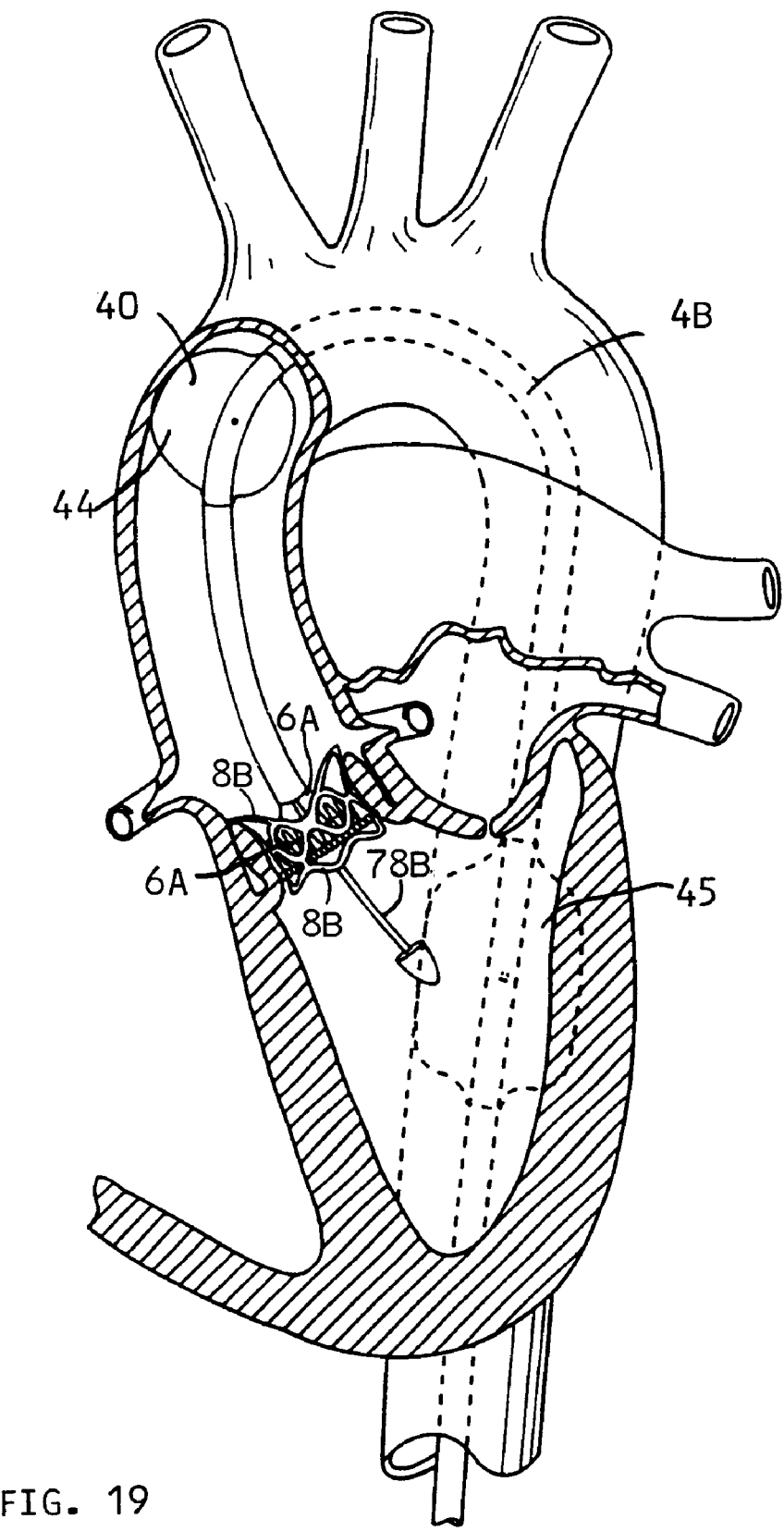
FIG. 19 shows the valve partially expanded with the catheter manipulated so that the valve engages the valve displacer.
Figure 20:
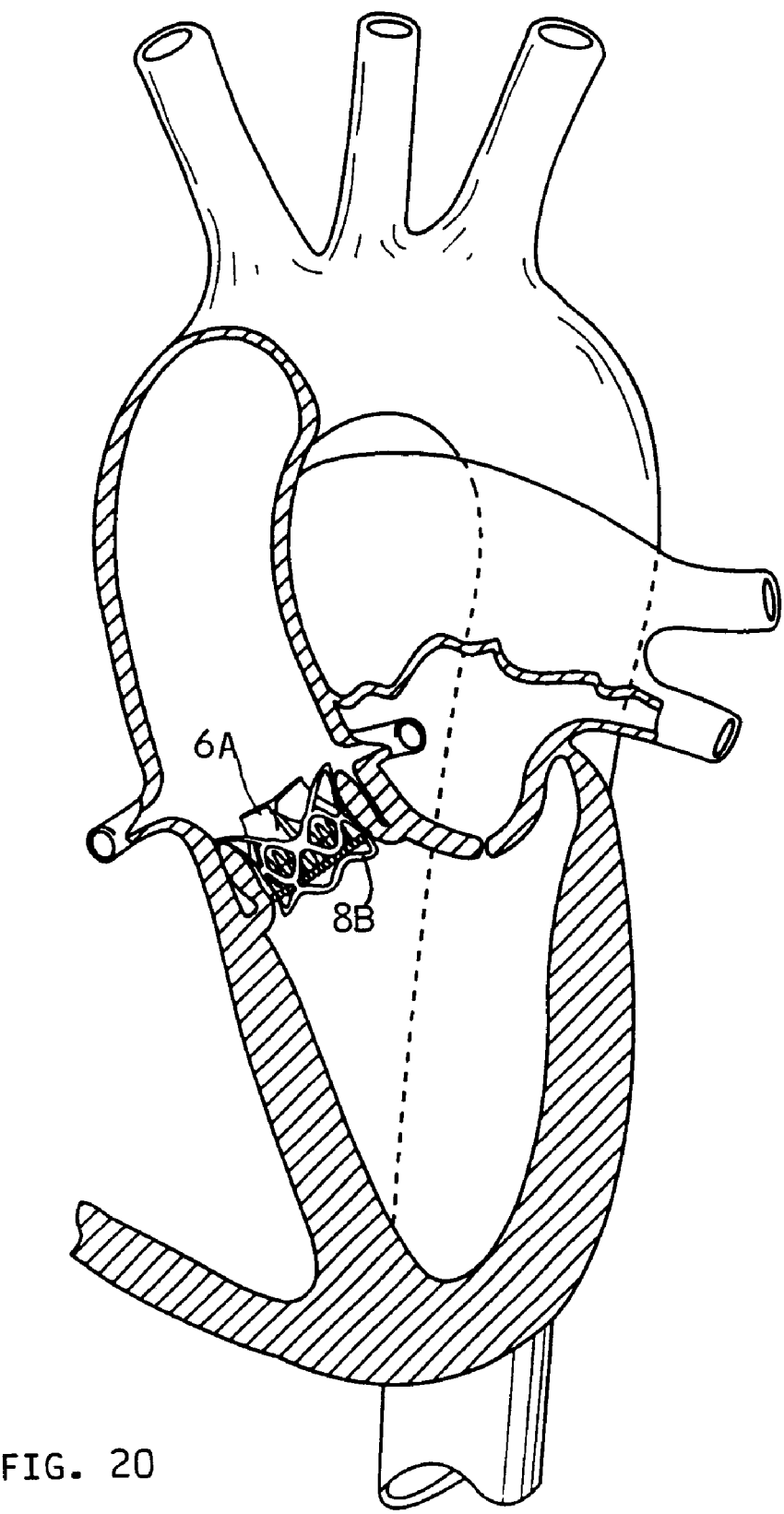
FIG. 20 shows the valve fully deployed and the catheter removed.
Figure 22:
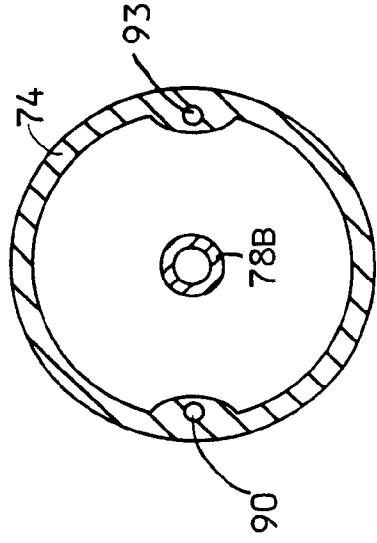
FIG. 22 is a cross-sectional view of the catheter along line C—C of FIG. 16.

Another method of implanting a cardiac valve is now described with reference to FIGS. 16–20 wherein the same or similar reference numbers refer to the same or similar structures. The method describes use of the delivery catheter 4B and cardiac valve 6A, however, the method may be practiced using other suitable structures. The delivery catheter 4B is introduced in any manner described above and is preferably introduced through the femoral artery. The guidewire 72 is advanced ahead of the catheter 4B into the ascending aorta and the delivery catheter 4B is advanced over the guidewire 72. The delivery catheter 4B is then advanced between the valve leaflets. A distal end of the valve displacer 8B is then advanced out of the chamber 76 and the catheter 4B is retracted until the valve displacer 8 contacts the valve opening. The catheter 4B is then retracted while the rod 78B is maintained in the same position so that the valve displacer 8B emerges from the chamber 76B as shown in FIG. 18. The catheter 4B is then advanced a predetermined amount and the rod is advanced to force a distal end of the valve 6A from the chamber 76B. The catheter 4B is then moved as necessary so that the protrusions 34 engage the openings 14 in the valve displacer 8 as shown in FIG. 19. The catheter 4B is then withdrawn further so that the support structure 26A expands to the fully deployed position of FIG. 20. The catheter 4B is then removed leaving the cardiac valve 6A as shown in FIG. 20 During the procedure described above, the temporary valve mechanism 40 provides temporary valve functions while the balloon 45 provides pumping assistance as described above.

Referring to FIGS. 23–30, another system 2C for implanting a cardiac valve 6C is shown. The system 2C includes the valve displacer 8 and delivery catheter 4 described above. The delivery catheter 4 has the balloon 50 for inflating the valve displacer 8, the balloon 52 for inflating a cardiac valve 6C, the temporary valve mechanism 40 and the balloon 45. The cardiac valve 6C is similar to the cardiac valves 6. 6A except that the cardiac valve 6C has barbs 100 which extend outwardly from the cardiac valve 6C in the expanded condition of FIG. 30. The barbs 100 secure the cardiac valve 6C to the valve displacer 8 or directly to the vessel wall. The cardiac valve 6C has depressions 102 so that the barbs 100 are recessed from an outer surface 104 of the cardiac valve 6C when in the collapsed position of FIG. 29. The depressions 102 prevent the barbs 100 from interfering with smooth retraction of the sheath 10. When the cardiac valve 6C is expanded, the depressions 102 and barbs 100 rotate and move outwardly to engage the valve displacer 8 or vessel wall.

Figure 24:
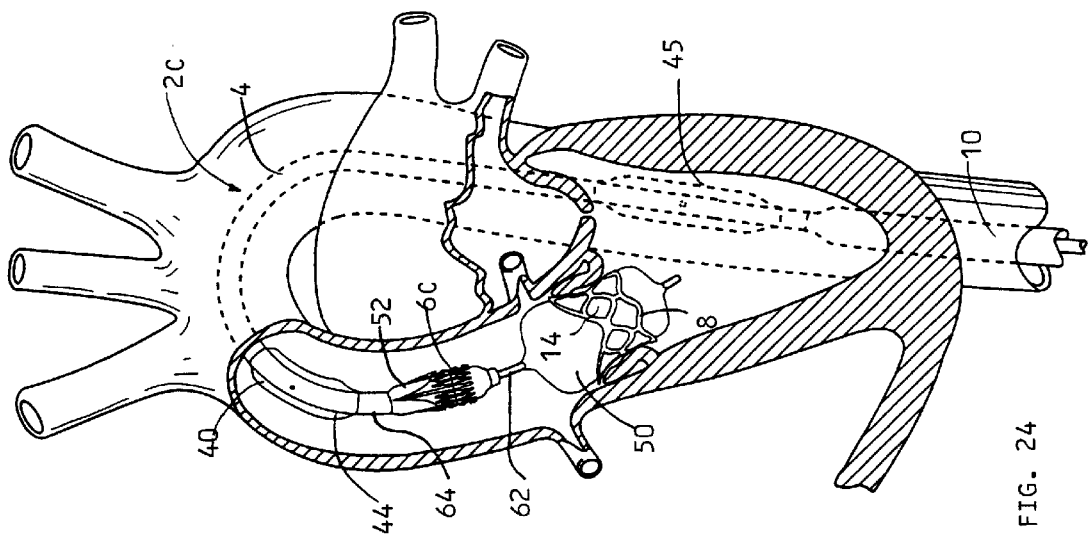
FIG. 24 shows the valve displacer expanded.
Figure 23:
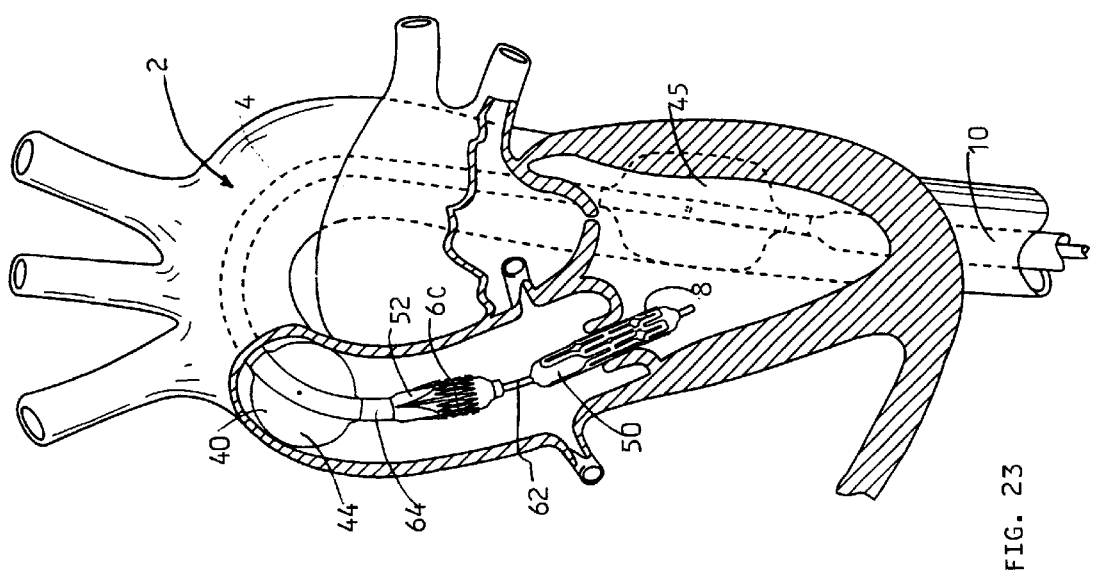
FIG. 23 shows another system for implanting a cardiac valve with the valve displacer positioned between the native leaflets.
Figure 26:
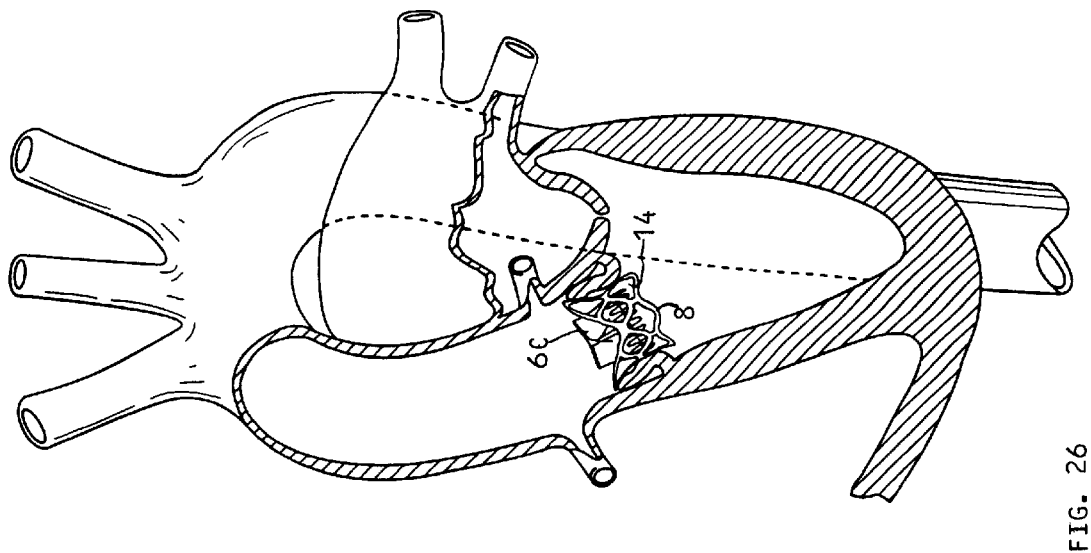
FIG. 26 shows the valve fully deployed within the valve displacer.
Figure 25:
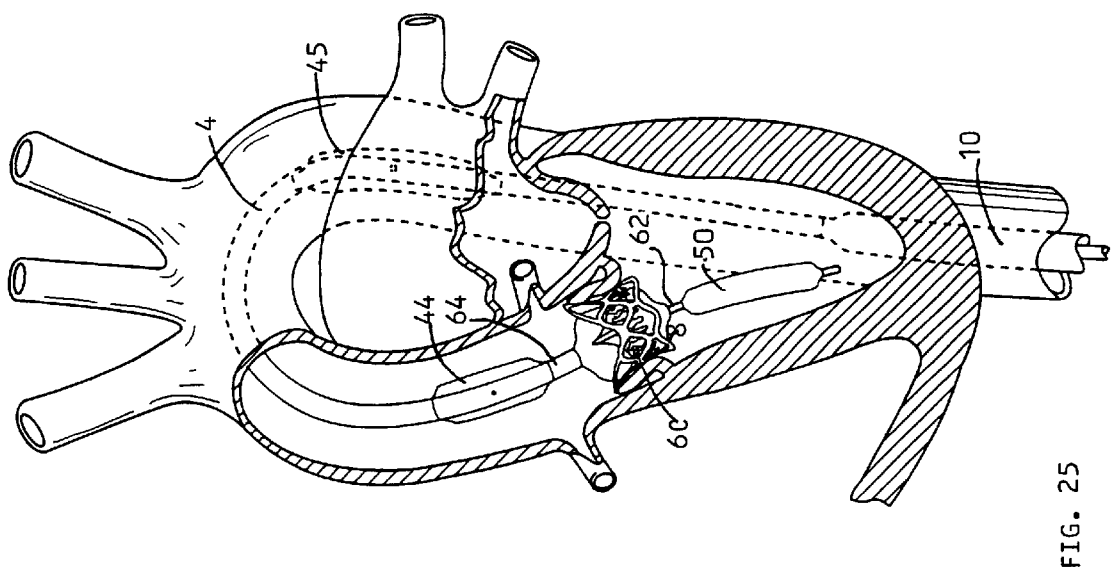
FIG. 25 shows the valve partially deployed within the valve displacer.

The system 2C is introduced into the patient in any manner described above and FIG. 23 shows the delivery catheter 4 passing through the femoral artery. The valve displacer 8 is deployed in the manner described above wherein the valve displacer 8 is introduced into the valve leaflets and expanded with the balloon 50 to hold the native leaflets open as shown in FIG. 24. The delivery catheter 4 may then be advanced so that the cardiac valve 6C is expanded in the valve displacer 8 with the barbs 100 passing into the openings 14 to secure the cardiac valve 6C to the valve displacer 8 as shown in FIGS. 25 and 26 The barbs 100 may be long enough to pierce and anchor in the native valve leaflets or may be designed to merely pass into and engage the sides of the openings 14.

Figure 27:
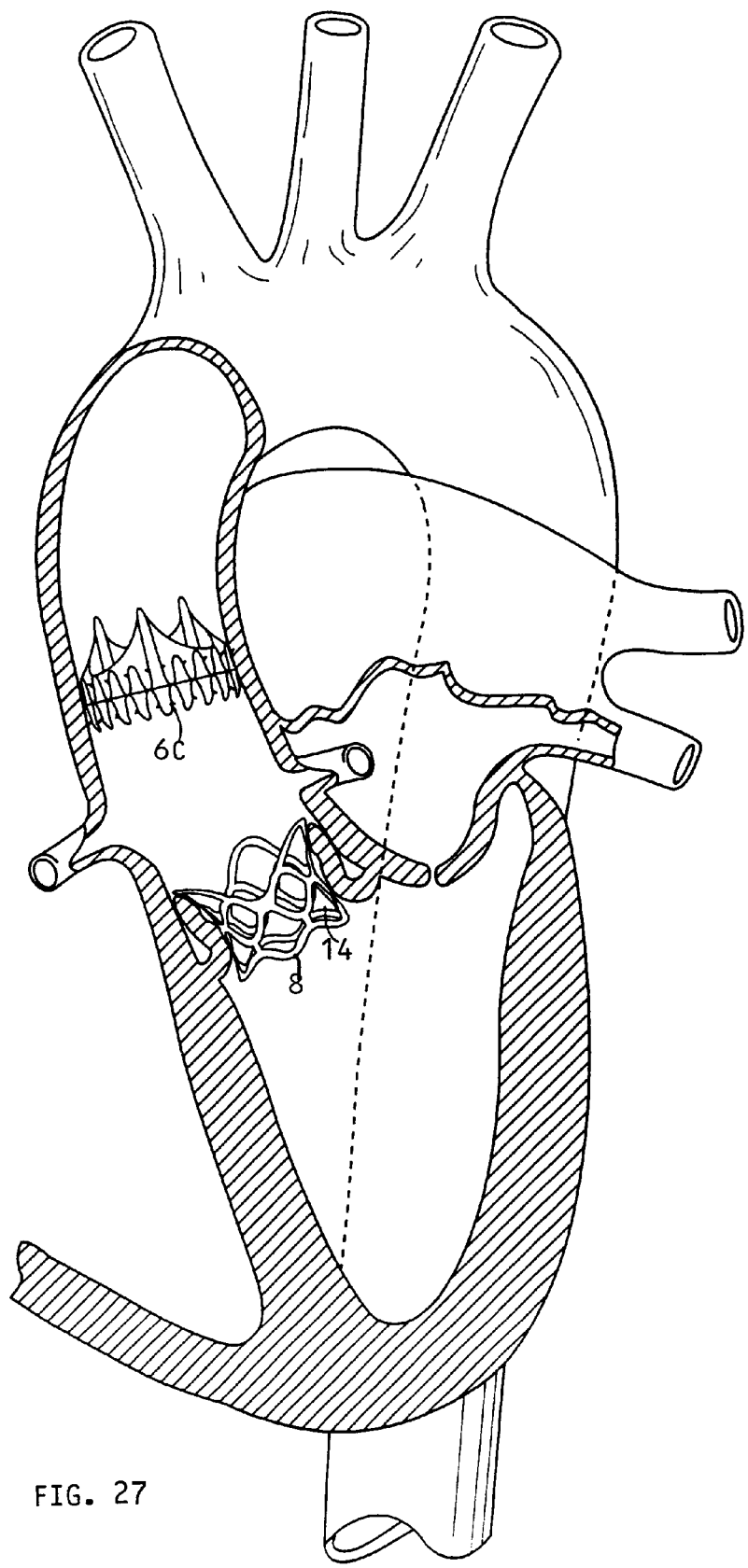
FIG. 27 shows the valve displacer holding the native leaflets open with the valve deployed in the ascending aorta.
Figure 28:
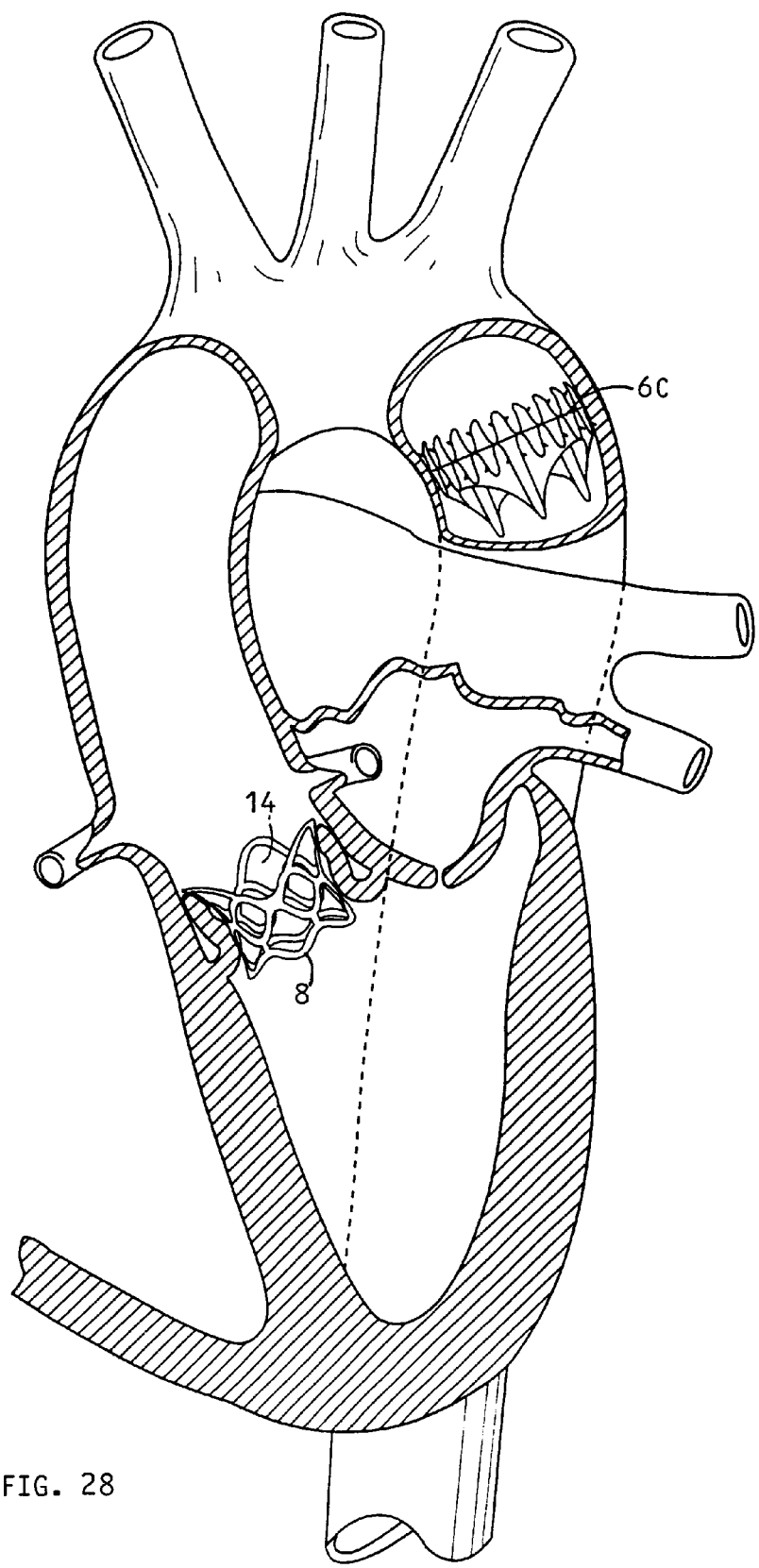
FIG. 28 shows the valve displacer holding the native leaflets open with the valve deployed in the descending aorta.

The term "cardiac valve" as used herein refers to a valve which substantially replaces the function of the patient's malfunctioning cardiac valve. The valve may be positioned in the native valve position or may be positioned in a different location while still substantially performing the functions of the native valve. For example, a replacement aortic valve may be positioned superior to the coronary ostia, in the aortic arch or in the descending aorta. Such a replacement valve will substantially function like the patient's native aortic valve. Referring to FIGS. 27 and 28 the cardiac valve 6C is deployed in the ascending and descending aorta with the barbs 100 securing the cardiac valve 6C directly to the vessel wall.

Referring to FIGS. 31–38 another system 2D for introducing a valve 6D is shown wherein similar or the same reference numbers refer to similar or the same structure. The valve 6D is coupled to a valve displacer 8D prior to introduction into the patient. The valve 6D has an expandable support structure 26D which is movable from the collapsed position of FIGS. 36 and 37 to the expanded position of FIGS. 34 and 35. The support structure 26D has flexible joints 106 which bend to radially collapse the support structure 26D. The support structure 26D has protrusions 34D which engage holes 108 in the valve displacer 8D. The valve 6D and valve displacer 8D may engage one another in any other suitable manner.

The valve 6D is inverted before being attached to the valve displacer 8D as shown in FIG. 35. A number of sutures 110, preferably three, are then passed through the valve 6D. The sutures 110 are used to invert the valve after introduction into the patient as will be explained below. The valve 6D may be any of the valves described herein or any other suitable valve without departing from the scope of the invention. A circumferential ring 111 extends around the support structure 26D. The ring 111 is preferably made of stainless steel or shape-memory alloy such as nitinol and provides circumferential support of the valve against the aortic wall for hemostasis.

The valve displacer 8D is mounted to a delivery catheter 4D having a balloon 112 for expanding the valve displacer 8D and valve 6D. The balloon 112 is coupled to a source of inflation fluid 114 (FIG. 31) for inflating the balloon 112. The catheter 4D passes through a trocar 116 having a hemostasis valve 117. The sutures 110 and the catheter 4D pass through the hemostasis valve which permits slidable movements of the sutures 110 and catheter 4D.

The valve 6D is preferably stored in a preservative solution until just before the procedure as shown in FIG. 34. The valve is then inverted as shown in FIG. 35 and the sutures 110 are passed through the valve 6D. The valve 6D is then attached to the valve displacer 8D as shown in FIG. 37 and mounted to the delivery catheter 4D.

Figure 31:
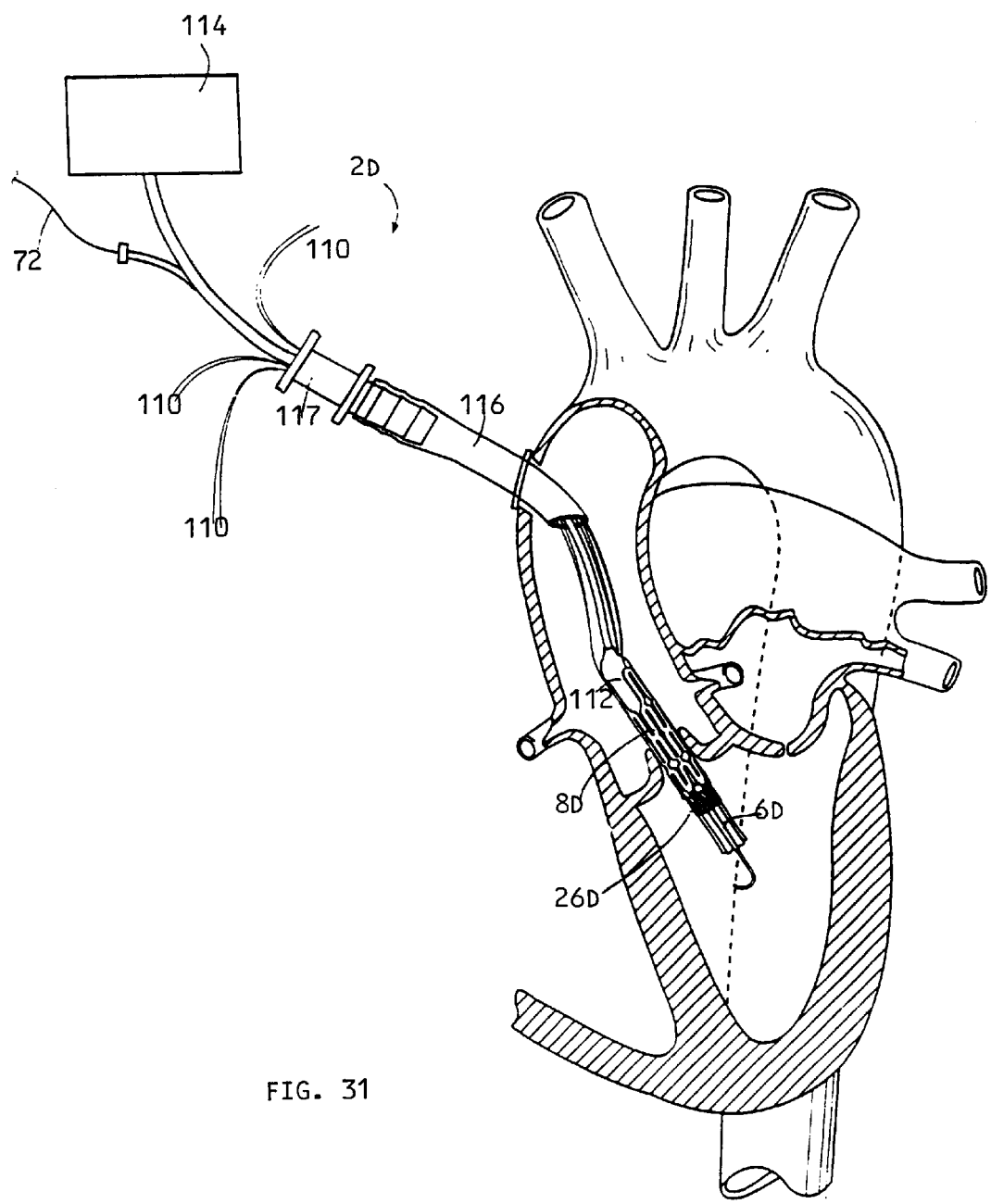
FIG. 31 shows another system for delivering a cardiac valve with the delivery catheter passing through a trocar in the ascending aorta.
Figure 32:
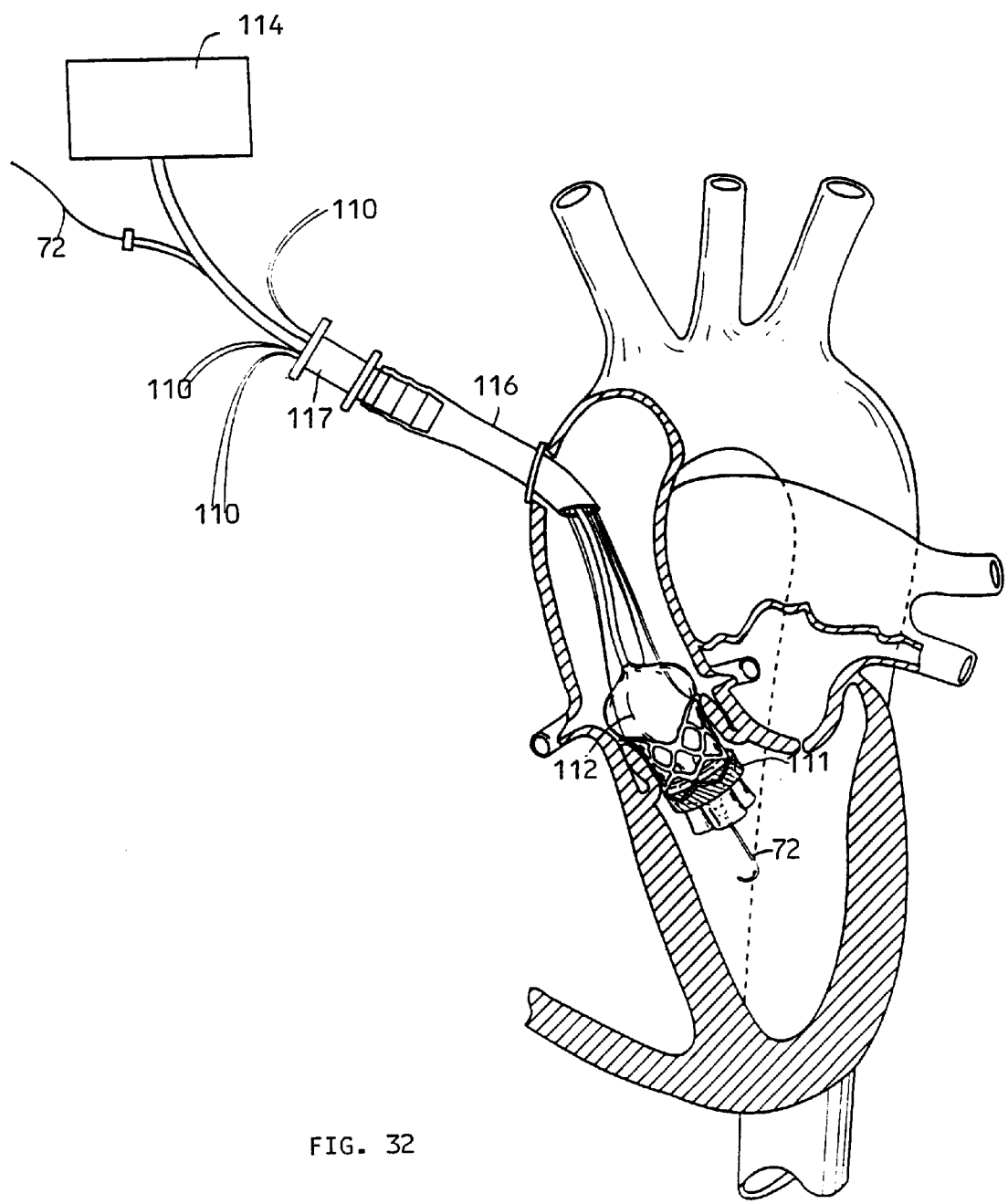
FIG. 32 shows an expansion mechanism expanding the valve displacer and the valve.

The valve 6D may be delivered in any manner described above and is preferably introduced through an incision in the patient's chest. Referring to FIGS. 31 and 32, the trocar 116 is introduced into the ascending aorta through purse-string sutures (not shown). The trocar 116 may have a chamber (not shown) in which the valve 6D is positioned when the trocar 116 is introduced into the ascending aorta. The sheath 10 (see FIGS. 1A, 1B and 2) described above may also be used to prevent contact between the valve and trocar and between the valve and the aortic wall. The valve 6D is preferably introduced with the patient's heart beating but may also be implanted with the patient's heart stopped and the patient supported by a bypass system. Although system 2D does not show the balloons 40 and 45, it is understood that the balloons 40, 45 may also be used with system 2D without departing from the scope. of the invention.

Figure 33:
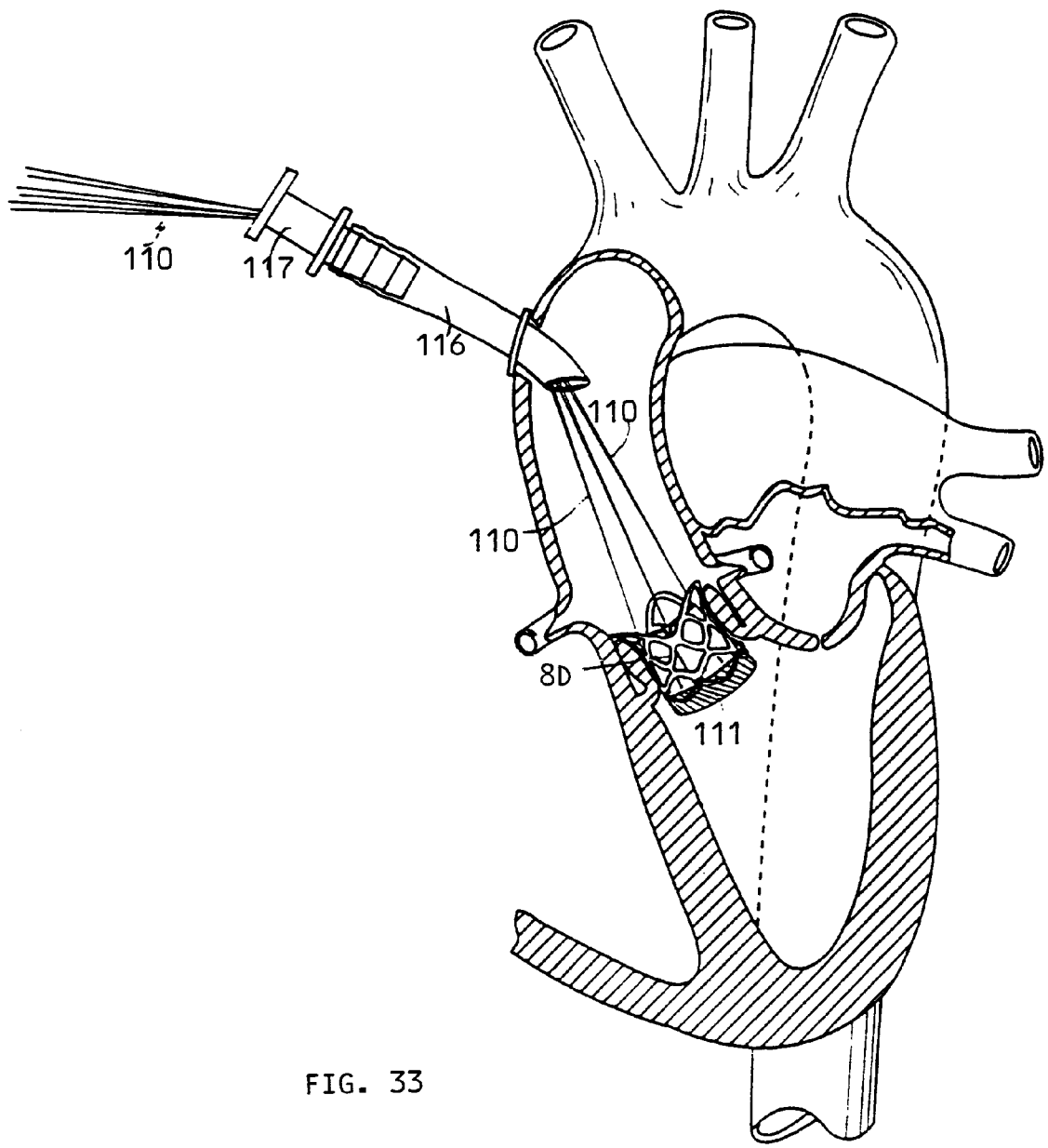
FIG. 33 shows sutures being pulled to invert the valve.
Figure 38:
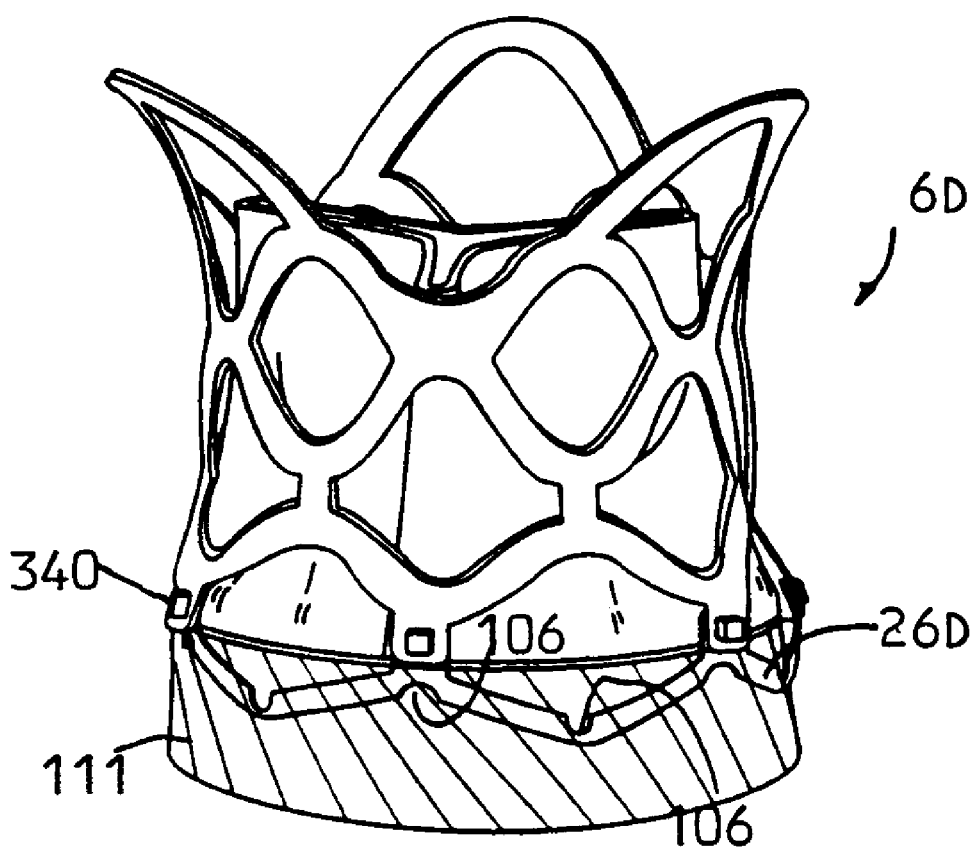
FIG. 38 shows the valve and the valve displacer in the expanded condition.

After introduction of the trocar 116, the valve 6D is advanced until the valve 6D is between the native valve leaflets. The balloon 112 is then inflated to expand the valve 6D and valve displacer 8D. The catheter 4D is then removed and the sutures 110 are pulled to invert the valve 6D as shown in FIG. 33. An end of each suture 110 is then pulled to remove the sutures 110. The trocar 116 and catheter 4D are then removed leaving the valve 6D (FIG. 38).

Although the foregoing invention has been described by way of illustration and example of preferred embodiments for purposes of clarity and understanding, changes and modifications to the preferred embodiments may be incorporated without departing from the scope of the invention. For example, the native valve may be removed rather than held open with the valve displacer, the replacement cardiac valve may be a completely synthetic or mechanical valve, and the expansion mechanism may be a mechanical mechanism rather than a balloon.

What is claimed is:

1. A method of implanting a cardiac valve, comprising the steps of:

introducing a replacement valve and a valve displacer into a patient, the replacement valve and valve displacer being mounted to a catheter and each being movable from a collapsed position to an expanded position, the replacement valve and valve displacer being introduced into the patient in the collapsed position;

positioning the valve displacer between valve leaflets of a native cardiac valve;

expanding the valve displacer to the expanded position after the positioning step, thereby displacing and holding the valve leaflets in an open position; and securing the replacement valve at a desired location in the patient wherein the replacement valve is secured to the valve displacer, said replacement valve having sharp elements which penetrate the native valve.

2. The method of claim 1, wherein:

the securing step is carried out with the valve interlocking with the valve displacer.

3. The method of claim 1, wherein:

the introducing step is carried out with the valve having a support structure and a valve portion, the support structure being expandable from a collapsed position to an expanded position, the introducing step being carried out with the support structure being in the collapsed position.

4. The method of claim 1, further comprising the step of:

enclosing the valve displacer in a flexible sheath during the introduction step; and uncovering the valve displacer before the expanding step.

5. The method of claim 1, wherein:

the introduction step is carried out with the catheter passing through a penetration in the aortic arch.

6. The method of claim 1, wherein:

the introducing step is carried out through the femoral artery.

7. The method of claim 1, wherein:

the introducing step is carried out with the valve being mounted on the catheter.

8. The method of claim 7, wherein:

the introducing step is carried out with the catheter having a valve mechanism.

9. The method of claim 8, wherein:

the introducing step is carried out the valve displacer having an end which flares outwardly when the valve displacer is in the expanded position.

10. The method of claim 7, wherein:

the introducing step is carried out with the catheter having a balloon, the balloon being coupled to a control mechanism for inflating and deflating the balloon to provide pumping assistance to the patient's heart.

11. The method of claim 1, wherein:

the introducing step is carried out with the catheter having an expandable member, the valve displacer being mounted to the expandable member.

12. The method of claim 1, wherein:

the introducing step is carried out with the catheter having an expandable member, the valve displacer being mounted to the expandable member.

13. The method of claim 1, wherein:

the introducing step is carried out with the valve displacer having a circumferential recess formed between a first end and a second end.

14. The method of claim 1, wherein:

the valve and valve displacement device are introduced together.

15. The method of claim 14, further comprising the step of:

inverting the valve after the introducing step.

16. The method of claim 1, wherein:

the valve introducing step is carried out with the valve having an expandable support structure, the expandable support structure having at least three posts extending from the expandable support structure.

* * * * *